United States Patent
Hongo et al.

(10) Patent No.: US 12,083,688 B2
(45) Date of Patent: Sep. 10, 2024

(54) INFORMATION PROCESSING APPARATUS, INFORMATION PROCESSING METHOD, AND INFORMATION PROCESSING PROGRAM

(71) Applicant: SONY CORPORATION, Tokyo (JP)

(72) Inventors: Kazuo Hongo, Chiba (JP); Toshimitsu Tsuboi, Tokyo (JP); Shunsuke Yajima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 609 days.

(21) Appl. No.: 17/281,739

(22) PCT Filed: Sep. 30, 2019

(86) PCT No.: PCT/JP2019/038507
§ 371 (c)(1),
(2) Date: Mar. 31, 2021

(87) PCT Pub. No.: WO2020/075553
PCT Pub. Date: Apr. 16, 2020

(65) Prior Publication Data
US 2021/0394365 A1 Dec. 23, 2021

(30) Foreign Application Priority Data

Oct. 11, 2018 (JP) .................................. 2018-192874

(51) Int. Cl.
*B25J 9/16* (2006.01)
*A61F 4/00* (2006.01)
(Continued)

(52) U.S. Cl.
CPC ............... *B25J 9/1697* (2013.01); *A61F 4/00* (2013.01); *G06V 40/10* (2022.01); *G10L 15/22* (2013.01)

(58) Field of Classification Search
None
See application file for complete search history.

(56) References Cited

U.S. PATENT DOCUMENTS

2009/0173560 A1* 7/2009 Nakamoto ............. B25J 9/1612
700/259
2013/0030570 A1 1/2013 Shimizu et al.
(Continued)

FOREIGN PATENT DOCUMENTS

CN 101952087 A 1/2011
CN 206925866 U 1/2018
(Continued)

OTHER PUBLICATIONS

Emrah Sisbot, A Human-Aware Manipulation Planner, Oct. 5, 2012, IEEE, vol. 28, p. 1054 (Year: 2012).*
(Continued)

*Primary Examiner* — Christian Chace
*Assistant Examiner* — Shayne M. Gilbertson
(74) *Attorney, Agent, or Firm* — Paratus Law Group, PLLC

(57) ABSTRACT

Provided is an apparatus for arranging objects in such a manner as to permit the user to handle the objects more easily. The information includes a robotic arm device configured to arrange one or more objects, and circuitry configured to determine one or more characteristics of a user, determine an arrangement position of each object of the one or more objects to be arranged based on the one or more determined characteristics of the user, and initiate control of the robotic arm device to arrange each object according to the determined arrangement position of the object.

19 Claims, 11 Drawing Sheets

(51) Int. Cl.
*G06V 40/10* (2022.01)
*G10L 15/22* (2006.01)

(56) References Cited

U.S. PATENT DOCUMENTS

| | | |
|---|---|---|
| 2015/0352719 A1 | 12/2015 | Nakazato et al. |
| 2016/0089782 A1* | 3/2016 | Sisbot ............... B25J 9/163 |
| | | 700/250 |
| 2018/0307966 A1* | 10/2018 | Ogawa ............ G05D 1/0227 |
| 2018/0317725 A1* | 11/2018 | Lee ................ B25J 15/0491 |
| 2020/0101614 A1* | 4/2020 | Thackston ........... B25J 13/006 |
| 2021/0170585 A1* | 6/2021 | Kim ............... B25J 11/0015 |

FOREIGN PATENT DOCUMENTS

| | | |
|---|---|---|
| CN | 107877516 A | 4/2018 |
| CN | 108481346 A | 9/2018 |
| JP | 2004-230509 A | 8/2004 |
| JP | 2007-160447 A | 6/2007 |
| JP | 2013022705 A | 2/2013 |
| JP | 2015230621 A | 12/2015 |
| JP | 2016068253 A | 5/2016 |
| KR | 101383450 B1 | 4/2014 |

OTHER PUBLICATIONS

Kyle Strabala, Toward Seamless Human-Robot Handovers, 2013, Journal of Human-Robot Interaction, vol. 2, No. 1, 2013, pp. 112-132 (Year: 2013).*

Andras Kupcsik, Learning Dynamic Robot-to-Human Object Handover from Human Feedback, Mar. 21, 2016 (Year: 2016).*

* cited by examiner

FIG. 3

| USER ID | PHYSICAL INFORMATION |
|---|---|
| U11 | UDA11 |
| U21 | UDA21 |
| U31 | UDA31 |
| U41 | UDA41 |
| ... | ... |

| USER ID | DATE | ARRANGEMENT INFORMATION |
|---|---|---|
| U11 | SEPTEMBER 25, 2018 | HDA11-1 |
| | JULY 13, 2018 | HDA11-2 |
| | ... | ... |
| U21 | ... | ... |
| U31 | ... | ... |
| U41 | ... | ... |
| ... | ... | ... |

108b

INFORMATION PROCESSING APPARATUS, INFORMATION PROCESSING METHOD, AND INFORMATION PROCESSING PROGRAM

CROSS REFERENCE TO PRIOR APPLICATION

This application is a National Stage Patent Application of PCT International Patent Application No. PCT/JP2019/038507 (filed on Sep. 30, 2019) under 35 U.S.C. § 371, which claims priority to Japanese Patent Application No. 2018-192874 (filed on Oct. 11, 2018), which are all hereby incorporated by reference in their entirety.

TECHNICAL FIELD

Embodiments of the present disclosure relate to an information processing apparatus, an information processing method, and an information processing program.

BACKGROUND ART

Proposed in recent years is a mobile manipulator robot that is configured by mounting a manipulator on a movable carriage.

Proposed, for example, in PTL 1 is a mobile robot that is configured by mounting a multi-joint manipulator on a movable carriage and adapted to do no harm to humans and goods around the mobile robot particularly while the mobile robot is running or while the multi-joint manipulator in a standby state is not activated.

Further, proposed in PTL 2 is a mobile robot that voluntarily receives goods from an acquisition source, carries the goods while inhibiting them from shaking by exercising vibration control, and certainly delivers the goods to a destination.

CITATION LIST

Patent Literature

[PTL 1]
Japanese Patent Laid-open No. 2004-230509
[PTL 2]
Japanese Patent Laid-open No. 2007-160447

SUMMARY

Technical Problem

However, the above-mentioned conventional technologies do not always arrange objects in such a manner as to permit a user to handle the objects more easily in consideration of physical information regarding the user.

In view of the above circumstances, the present disclosure proposes an information processing apparatus, an information processing method, and an information processing program that are capable of arranging objects in such a manner as to permit the user to handle the objects more easily.

Solution to Problem

According to an aspect of the present disclosure, there is provided an apparatus including: a robotic arm device configured to arrange one or more objects; and circuitry configured to determine one or more characteristics of a user, determine an arrangement position of each object of the one or more objects to be arranged based on the one or more determined characteristics of the user, and initiate control of the robotic arm device to arrange each object according to the determined arrangement position of the object.

According to another aspect of the present disclosure, there is provided a method of arranging one or more objects, the method including: determining one or more characteristics of a user; determining an arrangement position of each object of one or more objects to be arranged based on the one or more determined characteristics of the user; and controlling a robotic arm device to arrange each object according to the determined arrangement position of the object.

According to another aspect of the present disclosure, there is provided a non-transitory computer-readable storage medium having embodied thereon a program, which when executed by a computer causes the computer to execute a method, the method including: determining one or more characteristics of a user; determining an arrangement position of each object of one or more objects to be arranged based on the one or more determined characteristics of the user; and controlling a robotic arm device to arrange each object according to the determined arrangement position of the object

BRIEF DESCRIPTION OF DRAWINGS

FIG. 3 is a diagram illustrating an example of a storage section according to an embodiment of the present disclosure.

FIG. 4 is a diagram illustrating an example of the storage section according to an embodiment of the present disclosure.

DESCRIPTION OF EMBODIMENTS

Embodiments of the present disclosure will now be described in detail with reference to the accompanying drawings. The same parts in the embodiments described below are designated by the same reference signs and will not be redundantly described.

1. Overview of Information Processing

Figure 1:
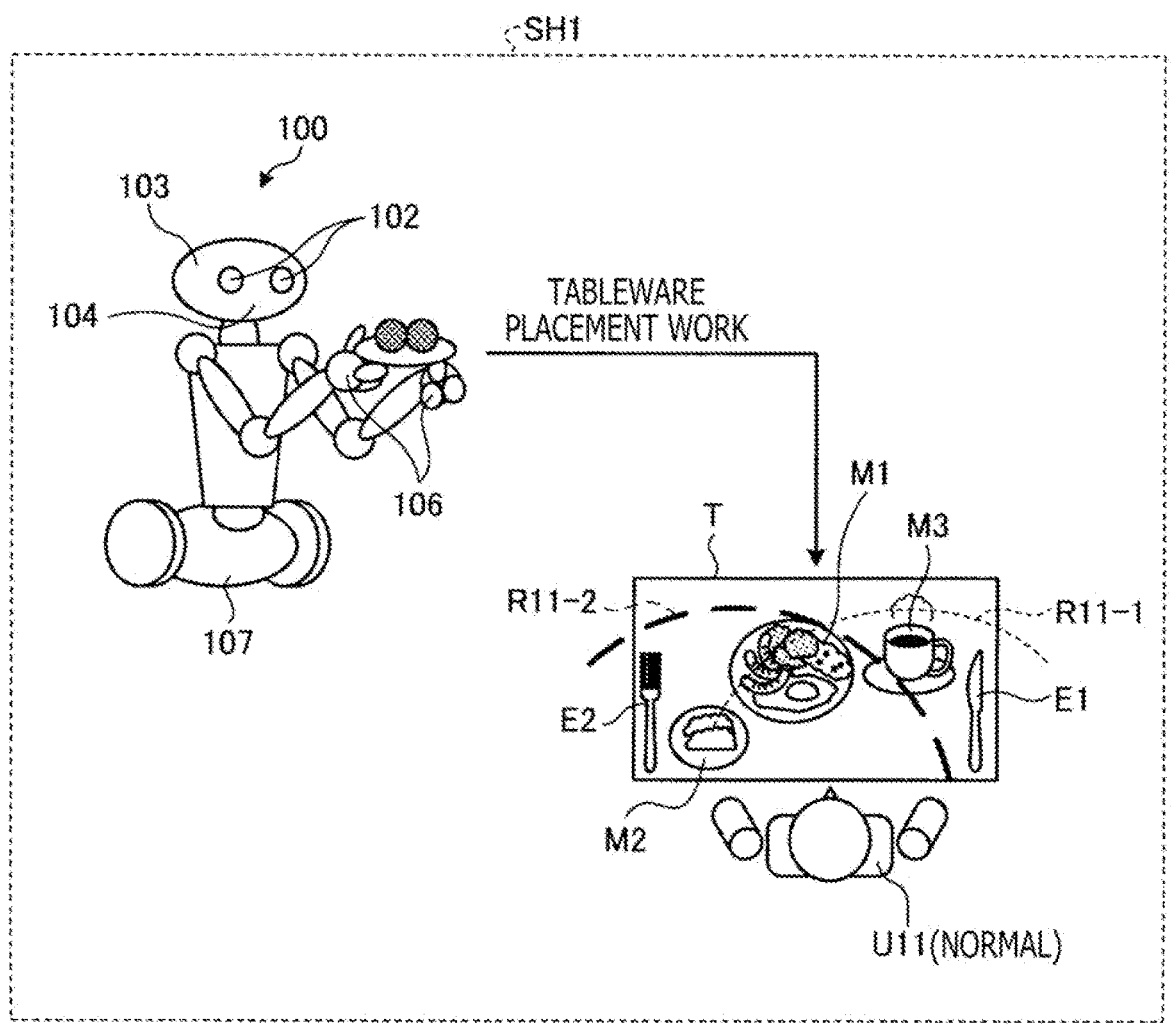
FIG. 1 is a diagram illustrating an example of information processing (pattern 1) according to an embodiment of the present disclosure.

First of all, an overview of information processing according to the present disclosure will be described with reference to FIG. 1. FIG. 1 is a diagram illustrating an example of information processing (pattern 1) according to the present disclosure. The information processing according to the present disclosure is performed by a robot apparatus 100 depicted in FIG. 1. In other words, the robot apparatus 100 is an example of an information processing apparatus according to the present disclosure. It should be noted that the external appearance of the robot apparatus 100 is not limited to the one depicted in FIG. 1.

In the example of FIG. 1, the robot apparatus 100 includes a camera 102, a microphone 103, an output section 104, a manipulator 106, and a drive section 107. The camera 102 is a processing section that is equivalent to the "eyes" of the robot apparatus 100 and captures an image of a target user and an image of a surrounding environment. The target user is a user to whom objects are to be delivered. Further, the microphone 103 is a processing section that is equivalent to the "ears" of the robot apparatus 100 and collects sounds. For example, the microphone 103 collects the sound of a voice uttered by the target user. Furthermore, the output section 104 is a processing section that is equivalent to the "mouth" of the robot apparatus 100 and, for example, outputs a voice as a response message with respect to the voice uttered by the target user. It should be noted that the output section 104 is also able to display (output) a response message or other predetermined information on a display screen (e.g., a display) instead of a voice. In such a case, although not depicted in FIG. 1, the robot apparatus 100 has a display screen, for example, on its trunk (equivalent to the "chest").

The manipulator 106 is a processing section that is equivalent to the "hands" of the robot apparatus 100 and used to grasp and move an object to the target user.

Therefore, the manipulator 106 is an example of a moving section. The drive section 107 is a processing section that is equivalent to the "legs" of the robot apparatus 100 and driven to move the robot apparatus 100 to the target user. Therefore, it can be said that the drive section 107 is also an example of the moving section. In the example of FIG. 1, the drive section 107 includes two wheels and a shaft for coupling the two wheels to one another. However, the configuration of the drive section 107 is not limited to the example of FIG. 1.

Prerequisites for information processing according to an embodiment will now be described. In a case where, for example, a user eats in a restaurant, it is preferable that the user be allowed to eat easily without having to stand up or forcibly move the body of the user while a number of tableware items are arranged within reach of the user and accessible by the user in a seated position. For example, depending on an order, food placed on a significantly large number of variously shaped plates and other tableware is placed. However, the larger the number of tableware items, the higher the probability of requiring the user to raise himself/herself and reach out for a distant tableware item. It is troublesome to repeat such work.

Further, in a case where a plurality of tableware items exists, it is necessary to pick up a target tableware item filled with desired food. In such an instance, a neighboring tableware item may interfere with the target tableware item. In some cases, therefore, it is difficult to pick up a target tableware item. For example, if tableware items are arranged close to each other while there is almost no space between them, it may be difficult to pick up a target tableware item due to an interruption by other tableware items. Furthermore, if, in such a situation, a tall tableware item such as a wine glass exists, it may be more difficult to pick up a target tableware item depending on the position where the wine glass is placed. Moreover, if the user is physically disabled, for example, injured in his/her arm or unable to properly bend down, the user finds it more difficult to perform the above-described work. Consequently, the user hopes that tableware items be arranged in such a manner as to permit the user to easily pick up a target tableware item.

In view of the above-described circumstances, it is demanded that the positions where objects (tableware items in the above example) are arranged be adjusted so as to maximize the ease of operation by simulating, for example, possible motions of a human body.

In order to meet the above-mentioned prerequisites and solve the above-described problem, the robot apparatus 100 according to an embodiment performs the following information processing and operations related to the information processing. More specifically, the robot apparatus 100 acquires physical information regarding a target user to whom objects are to be delivered, and determines, on the basis of the physical information regarding the target user, the positions where the objects are to be arranged at the time of delivery of the objects to the target user. For example, the robot apparatus 100 determines the arrangement positions of the objects in accordance with a range that permits the target user to move his/her body and is based on the physical information regarding the target user.

The physical information regarding the target user may include information regarding, for example, age, an arm length, a dominant arm, physical disability, and a possible upper body inclination amount, but need not be limited to such information.

An example of information processing will now be described with reference to the example of FIG. 1. An embodiment described below, including the example of FIG. 1, assumes that the target user eats in a restaurant SH1. Therefore, the robot apparatus 100 determines the placement positions (exemplary arrangement positions) of objects, namely, plates filled with food and tableware items such as eating utensils (knives, forks, etc.), at the time of placement on a table T. Further, both the plates and eating utensils may be simply referred to as the "tableware." Furthermore, the example of FIG. 1 assumes that the user to whom the tableware is delivered (the user who eats) is the target user U11. Moreover, the example of FIG. 1 depicts an example of pattern 1, which is the most common pattern of information processing for determining the arrangement positions.

First of all, when the target user U11 takes a seat at the table T, the robot apparatus 100 moves to the seat of the target user U11 and takes an order. The example of FIG. 1 assumes that the robot apparatus 100 has received an order for a main dish, a side dish (bread), and another side dish (coffee). It is also assumed that the robot apparatus 100 has a database indicative of the relationship of ordered meals to associated plates and eating utensils.

Further, when receiving an order, the robot apparatus 100 uses the camera 102 to image the target user U1, and identifies physical information regarding the target user U11 in accordance with imaged information acquired by an imaging operation. Then, on the basis of the identified physical information, the robot apparatus 100 determines whether or not there are necessary considerations to be taken into account as regards the placement positions of tableware items. The example of FIG. 1 assumes that the robot apparatus 100 has identified, on the basis of the imaged information, age, an arm length, and a dominant arm of the target user U11 who is determined to be "in his/her twenties," has the arm length of "L11 (cm)," and is "right-handed." Furthermore, it is assumed that the robot apparatus 100 has determined, on the basis of the imaged information, that the target user U11 is not particularly injured and therefore has determined that the target user U11 is "healthy." Moreover, as the target user U11 is "healthy," the robot apparatus 100 determines that no considerations need to be taken into account regarding the placement positions of tableware items.

It should be noted that the robot apparatus 100 is also able to identify the physical information on the basis not only of the imaged information but also of speech information collected by the microphone 103. For example, in a case where the target user U11 has uttered, "My right arm is injured," the robot apparatus 100 determines that the target user U11 is injured in his/her right arm and is thus an "injured" person, and that some considerations need to be taken into account regarding the placement positions of tableware items.

After determining that no considerations need to be taken into account regarding the placement positions of tableware items, the robot apparatus 100 determines the placement positions of tableware items in accordance with general rules. The general rules concerning the tableware placement positions of tableware M1 for a main dish, tableware M2 for a side dish (bread), tableware M3 for a side dish (coffee), tableware E1 (knife), and tableware E2 (fork) would suggest you to place the tableware M1 at the center of the table T, place the tableware M2 on the left of the tableware M1, place the tableware M3 on the right of the tableware M1, place the tableware E1 at the rightmost position, and place the tableware E2 at the leftmost position. Therefore, the robot apparatus 100 determines the detailed arrangement positions for arranging the tableware M1, tableware M2, tableware M3, tableware E1, and tableware E2 in the above-described positional relationship. It should be noted that, if the positional relationship between the tableware items to be placed on the table T is predetermined by the restaurant SH1, the robot apparatus 100 may adopt such a predetermined positional relationship.

In accordance with the range that permits the target user U11 to move his/her body and is based on the physical information regarding the target user U11, the robot apparatus 100 determines the tableware placement positions. For example, as the arm length of the target user U11 is "L11 (cm)," the robot apparatus 100 identifies an arm movable range based on the arm length "L11 (cm)," and determines the tableware placement positions within the identified arm movable range. In the example of FIG. 1, a region R11-1, which is enclosed by an arc-shaped dotted line, indicates the movable range of a right arm. The target user U11 in a seated position is unable to reach the outside of the region R11-1 even when his/her right arm is fully extended. Further, in the example of FIG. 1, a region R11-2, which is enclosed by an arc-shaped dotted line, indicates the movable range of a left arm. The target user U11 in a seated position is unable to reach the outside of the region R11-2 even when his/her left arm is fully extended.

After identifying the above-mentioned regions, the robot apparatus 100 determines the tableware placement positions within a range including the region R11-1 and the region R11-2 in accordance with the general rules. More specifically, as illustrated in FIG. 1, the robot apparatus 100 determines the arrangement positions within the range including the region R11-1 and the region R11-2 so as to place the tableware M1 at the center, place the tableware M2 on the left of the tableware M1, place the tableware M3 on the right of the tableware M1, place the tableware E1 at the rightmost position, and place the tableware E2 at the leftmost position. In the example of FIG. 1, as the target user U11 is "right-handed," the robot apparatus 100 has determined a placement of the tableware E1 at the rightmost position and the tableware E2 at the leftmost position. However, in a case where the target user U11 is "left-handed," for example, the robot apparatus 100 determines a placement of the tableware E1 at the leftmost position and the tableware E2 at the rightmost position.

Further, the robot apparatus 100 is also able to determine the tableware placement positions in accordance with contents of tableware. For example, the tableware M3 is a coffee cup filled with hot dangerous coffee. Therefore, if the tableware M3 is placed immediately in front of the target user U11, a dangerous situation may arise. Consequently, as illustrated in FIG. 1, the robot apparatus 100 determines the tableware placement positions so as to place the tableware M3 at a relatively distant position within the region R11-1.

After determining the tableware placement positions as illustrated in FIG. 1, the robot apparatus 100 perform actual tableware placement work in accordance with the determined tableware placement positions. When, for example, placing the tableware M1, the tableware M2, the tableware M3, the tableware E1, and the tableware E2 one by one, the robot apparatus 100 determines the order of tableware placement and perform tableware placement work in the determined order. For example, in a case where the tableware M1 is the first tableware to be placed, the robot apparatus 100 grasps the tableware M1 filled with food and then moves to the table T. Subsequently, the robot apparatus 100 places the tableware M1 at the approximate center of the table T in accordance with the above-mentioned determined tableware placement positions. The description of the placement of the remaining tableware items is omitted because they are placed in sequence.

As described above, the robot apparatus 100 according to an embodiment acquires the physical information regarding the target user to whom objects are to be delivered, and determines object arrangement positions at the time of delivery of the objects to the target user on the basis of the acquired physical information regarding the target user. This enables the robot apparatus 100 to arrange the objects in such a manner as to permit the user to handle the objects more easily in consideration of the physical information regarding the user. Further, according to the example of FIG. 1, the robot apparatus 100 is able to arrange tableware in such a manner as to permit the user to handle the tableware easily. Furthermore, as a result of this, the robot apparatus 100 is able to permit the user to enjoy eating comfortably at ease.

It should be noted that the example of FIG. 1 is described on the assumption that the information processing according to an embodiment is performed by the robot apparatus 100. In reality, however, the information processing is performed by a control section 109 depicted in FIG. 2. Therefore, it can be said that the control section 109 (or an apparatus equivalent to the control section 109) functions as the information processing apparatus according to the present disclosure.

2. Configuration of Robot Apparatus

Figure 2:
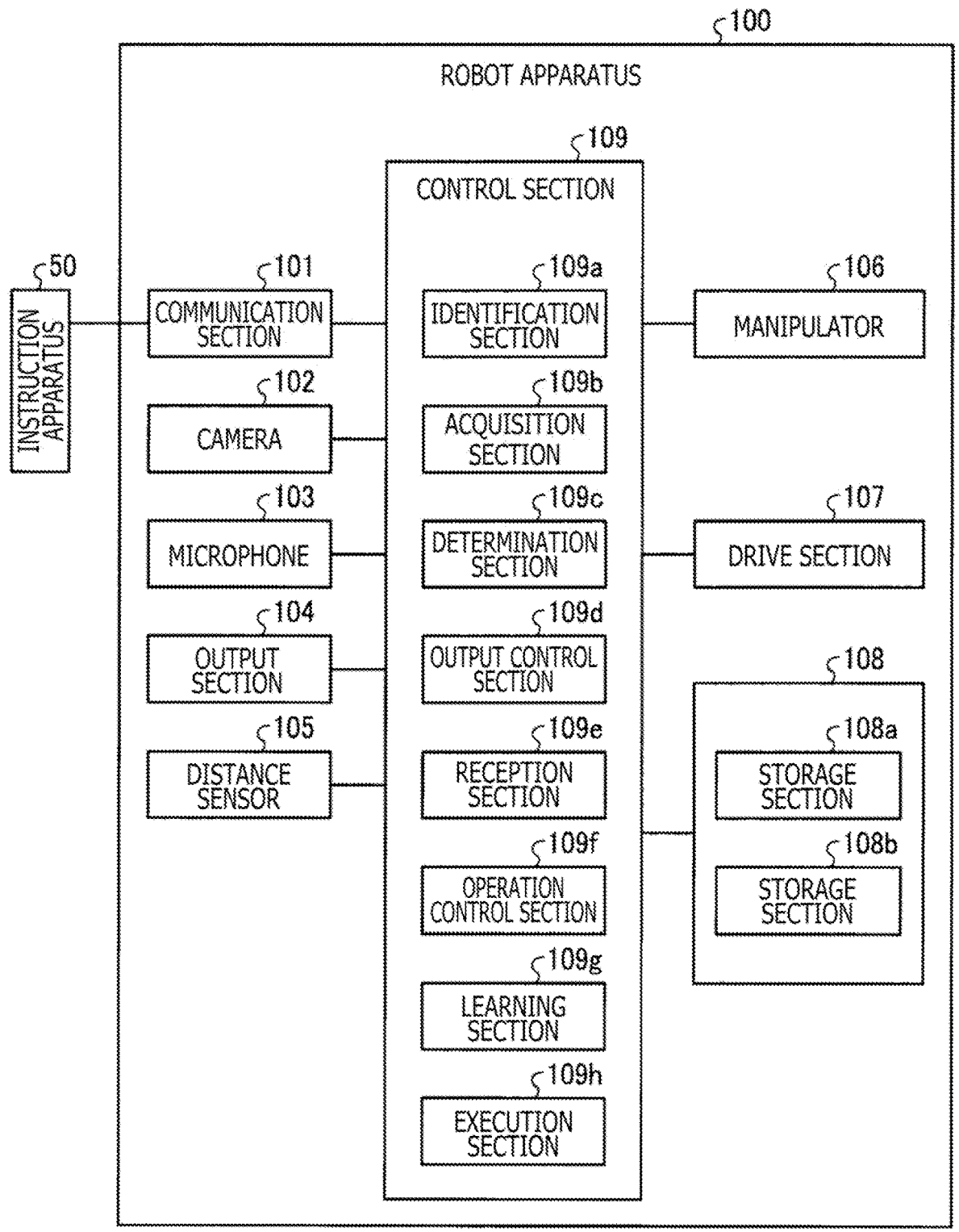
FIG. 2 is a schematic diagram illustrating a functional configuration for controlling a robot apparatus according to an embodiment of the present disclosure.

A configuration of the robot apparatus 100 according to an embodiment will now be described with reference to FIG. 2. FIG. 2 is a schematic diagram illustrating a functional configuration for controlling the robot apparatus 100 according to an embodiment of the present disclosure. As illustrated in FIG. 2, the robot apparatus 100 includes a communication section 101, a camera 102, a microphone 103, an output section 104, a distance sensor 105, a manipulator 106, a drive section 107, a storage section 108, and a control section 109.

(Communication Section 101)

The communication section 101 is implemented, for example, by an NIC (Network Interface Card). The communication section 101 is wiredly or wirelessly connected to a network and transmits and receives information, for example, to and from an instruction apparatus 50.

(Camera 102)

The camera 102 is a processing section that is equivalent to the "eyes" of the robot apparatus 100 and captures an image of the target user to whom objects are to be delivered and an image of a surrounding environment. For example, when the robot apparatus 100 receives an order from the target user, the camera 102 captures an image of the whole body of the target user.

Further, the camera 102 is able to store, in a storage section (not depicted), imaged information acquired by an imaging operation. Furthermore, the camera 102 transmits the imaged information to the control section 109.

(Microphone 103)

The microphone 103 is a processing section that is equivalent to the "ears" of the robot apparatus 100 and collects sounds. For example, the microphone 103 collects the sound of a voice uttered by the target user. When, for example, the robot apparatus 100 receives an order from the target user, the microphone 103 collects the sound of a voice uttered by the target user. Further, the microphone 103 is able to store, in the storage section (not depicted), utterance information acquired by collecting a sound. Furthermore, the microphone 103 transmits the imaged information to the control section 109.

(Output Section 104)

The output section 104 is a processing section that is equivalent to the "mouth" of the robot apparatus 100 and, for example, outputs a voice as a response message with respect to the voice uttered by the target user. It should be noted that the output section 104 is also able to display (output) a response message or other predetermined information on a display screen (e.g., a display) instead of a voice.

(Distance Sensor 105)

The distance sensor 105 measures the distance from the robot apparatus 100 to an object, and transmits the measured distance to the control section 109.

(Manipulator 106)

The manipulator 106 is a processing section that is equivalent to the "hands" of the robot apparatus 100 and used to grasp and move an object to the target user.

(Drive Section 107)

The drive section 107 is a processing section that is equivalent to the "legs" of the robot apparatus 100 and driven to move the robot apparatus 100 to the target user. It should be noted that the control section 109 controls the drive section 107 to thereby move the robot apparatus 100 in a selected direction (to a selected destination).

(Storage Section 108)

The storage section 108 is implemented by a semiconductor memory element, such as a RAM (Random Access Memory) or a flash memory, or a storage apparatus, such as a hard disk or an optical disk. The storage section 108 includes a storage section 108*a* and a storage section 108*b*.

(Storage Section 108*a*)

The storage section 108*a* stores physical information regarding the body of the target user to whom objects are to be delivered. For example, a later-described identification section 109*a* identifies the physical information regarding the body of the target user, and stores the identified physical information in the storage section 108*a*. FIG. 3 illustrates an example of the storage section 108*a* according to an embodiment of the present disclosure. In the example of FIG. 3, the storage section 108*a* has a "user ID" field and a "physical information" field.

The "user ID" represents identification information for identifying a target user. For example, in a case where the target user has a terminal apparatus (e.g., a smartphone) and is ready to communicate with the robot apparatus 100, the "user ID" may be identification information for identifying the terminal apparatus of the target user. The "physical information," which is physical information regarding the body of the target user, represents physical information that is identified on the basis of information acquired by various sensors (e.g., the camera 102 and the microphone 103). It should be noted that although the example of FIG. 3 uses conceptual signs such as "UDA11" as the physical information, the physical information is, in reality, text or other information indicative of a physical condition, for example.

More specifically, FIG. 3 depicts an example in which the physical information regarding a target user (target user U11) identified by the user ID "U11" is "UDA11."

(Storage Section 108*b*)

The storage section 108*b* stores information regarding arrangement positions determined for the target user. For example, a later-described determination section 109*c* determines the object arrangement positions for the target user, and stores information indicative of the determined object arrangement positions in the storage section 108*b*. FIG. 4 illustrates an example of the storage section 108*b* according to an embodiment of the present disclosure. In the example of FIG. 4, the storage section 108*b* has a "user ID" field, a "date" field, and an "arrangement information" field.

The "user ID" represents identification information for identifying a target user. For example, in a case where the target user has a terminal apparatus (e.g., a smartphone, etc.) and is ready to communicate with the robot apparatus 100, the "user ID" may be identification information for identifying the terminal apparatus of the target user. The "date" represents a date when arrangement positions are determined. In the example of FIG. 1, it can be said the "date" is a date when the target user took a meal in the restaurant SH1. The "arrangement information" represents information indicative of arrangement positions determined for the target user. It should be noted that although the example of FIG. 4 uses conceptual signs such as "HDA11-1" as the arrangement information, the arrangement information is, in reality, image information indicative of the arrangement positions, for example.

More specifically, FIG. 4 depicts an example in which the arrangement positions indicated by "HDA11-1" are determined on a date of "Sep. 25, 2018" for a target user (target user U11) identified by the user ID "U11." It should be noted that the storage section 108b is also able to store instruction information indicative of an instruction regarding the arrangement positions and received from the target user.

(Control Section 109)

Returning to FIG. 2, the control section 109 is implemented when various programs stored in a storage apparatus in the robot apparatus 100 are executed in a work area of a RAM, for example, by a CPU (Central Processing Unit) or an MPU (Micro Processing Unit).

Further, the control section 109 is also implemented by an integrated circuit such as an ASIC (Application Specific Integrated Circuit) or an FPGA (Field Programmable Gate Array).

As illustrated in FIG. 2, the control section 109 includes an identification section 109a, an acquisition section 109b, a determination section 109c, an output control section 109d, a reception section 109e, an operation control section 109f, a learning section 109g, and an execution section 109h, and implements or performs information processing functions and operations described below. The internal configuration of the control section 109 is not limited to the one depicted in FIG. 2. The control section 109 may adopt any other configuration that performs later-described information processing. Further, the connections between the processing sections included in the control section 109 are not limited to those depicted in FIG. 2. Different connections may be made between the processing sections included in the control section 109.

(Identification Section 109a)

The identification section 109a identifies physical information regarding the body of a target user to whom objects are to be delivered. The physical information to be identified by the identification section 109a includes information regarding, for example, age, an arm length, a dominant arm, physical disability, and a possible upper body inclination amount, but is not limited to such information. For example, the identification section 109a identifies the physical information regarding the target user in accordance with information acquired by various sensors (e.g., the camera 102 and the microphone 103). Further, it can be said that the identification section 109a identifies physical characteristics or properties of the target user to acquire the physical information indicative of the identified physical characteristics or properties. In the example of FIG. 1, on the basis of imaged information obtained by capturing an image of the target user U1 with the camera 102, the identification section 109a has identified, as the physical characteristics, the age, the arm length, and the dominant arm of the target user U11 who is determined to be "in his/her twenties," has an arm length of "L11 (cm)," and is "right-handed."

Additionally, the identification section 109a identifies the health condition of the target user on the basis of the identified physical characteristics. In the example of FIG. 1, the identification section 109a has not identified, for example, any injury in particular on the basis of the imaged information. Therefore, the identification section 109a identifies the health condition of the target user U11 by determining that the target user U11 is "healthy." Meanwhile, in a case where, for example, an injury is recognized on the basis of the imaged information, the identification section 109a identifies the health condition of the target user U11 by identifying (determining) that the target user U11 is "injured" (or injured, for example, in his/her right arm).

Further, the identification section 109a is also able to identify the physical information by using not only the imaged information but also the speech information collected by the microphone 103. For example, in a case where the target user U11 has uttered, "My right arm is injured," the identification section 109a determines that the target user U11 is physically disabled, namely, "injured in his/her right arm." Furthermore, in such a case, the identification section 109a identifies the health condition of the target user U11 by identifying (determining) that the target user U11 is "injured" (or injured, for example, in his/her right arm). It should be noted that the health condition according to an embodiment is recognizable as physical information.

Moreover, the identification section 109a is able to identify not only the physical information but also the condition of an object. For example, the identification section 109a identifies the condition of an object by determining, for example, the temperature of the object, the shape of the object, the size of the object, and the contents of the object. In a case where the tableware placement positions are to be determined in accordance with food as illustrated in FIG. 1, the identification section 109a identifies the tableware to be used for each food on the basis of, for example, an order received from the target user. As regards the identified tableware, the identification section 109a then identifies the temperature, shape, size, and contents (i.e., food) of the tableware to be filled with meal. In a case where the association between each food and the tableware to be used is stored in a storage section, the identification section 109a references the storage section to identify the tableware and its temperature, shape, and size. Further, the identification section 109a transmits the above identified information to the acquisition section 109b.

Moreover, the identification section 109a may identify the physical information and the condition of an object on the basis of not only the information acquired by the camera 102 and microphone 103 but also sensor information acquired by various sensors. The various sensors include an infrared camera, a thermographic sensor, and a ToF (Time of Flight) sensor. These sensors are generally mounted on the head of the robot apparatus 100. Obviously, however, these sensors may be mounted on a different part (e.g., the manipulator 106).

Additionally, in a case where a sensor (e.g., a surveillance camera installed in the restaurant SH1) is installed, for example, in an environment surrounding the robot apparatus 100 and capable of communicating with the robot apparatus 100, the identification section 109a may use information acquired by such a sensor.

(Acquisition Section 109b)

The acquisition section 109b acquires physical information regarding the body of the target user to whom objects are to be delivered. For example, the acquisition section 109b acquires, as the physical information, at least one of information items indicative of age, an arm length, a dominant arm, physical disability, or a possible upper body inclination amount. The acquisition section 109b acquires the physical information, for example, from the storage section 108b. Further, the acquisition section 109b may directly acquire the physical information from the identification section 109a. Furthermore, the acquisition section 109b additionally acquires information regarding the health condition and the condition of an object, which are identified by the identification section 109a. Moreover, the acquisition section 109b acquires, as the physical information, physical information outputted by a model (a later-described model MD1) that is generated by learning the relationship between the external appearance of the target user and the physical information regarding the target user. It should be noted that the identification section 109a may double as the acquisition section 109b.

(Overview (1) of Determination Section 109c)

The determination section 109c determines the arrangement positions of objects at the time of delivery of the objects to the target user on the basis of the physical information regarding the target user. More specifically, the determination section 109c determines the object arrangement positions in accordance with a range that permits the target user to move his/her body and is based on the physical information. As mentioned earlier, the identification section 109a identifies the physical information regarding the body of the target user (physical characteristics, physical properties, and health condition). Then, on the basis of the physical information identified by the identification section 109a, the determination section 109c determines the object arrangement positions at the time of delivery of the objects to the target user.

(Determination Processing Pattern 1)

First of all, determination processing performed in a case where the identification section 109a has identified (determined) that the target user is healthy and does not have a physical disability such as an injury will be described as determination processing pattern 1. Determination processing pattern 1 is already described with reference to FIG. 1. Therefore, the description of determination processing pattern 1 will be partially omitted.

For explanation purposes, the determination processing is divided into some patterns depending on the situation. An example of each determination processing pattern is described below. Further, as illustrated in FIG. 1, it is assumed that the determination processing is performed in a situation where tableware placement positions are to be determined in accordance with a meal. Furthermore, in each pattern, the target user U11 is mainly used as the target user. However, it is well to remember that, for convenience of explanation, different physical information is identified as regards the target user U11.

The identification section 109a identifies the physical information regarding the target user U11 on the basis of imaged information acquired by an imaging operation. The example of FIG. 1 assumes that the identification section 109a has identified, on the basis of the imaged information, the age, the arm length, and the dominant arm of the target user U11 who is determined to be "in his/her twenties," has an arm length of "L11 (cm)," and is "right-handed." Further, it is assumed that the identification section 109a has identified, on the basis of the imaged information, that the target user U11 is "healthy" because no particular injury or other health problems have been identified.

In the above case, the determination section 109c first determines that no considerations need to be taken into account regarding the tableware placement positions because the target user U11 is "healthy." After determining that no considerations need to be taken into account regarding the tableware placement positions, the determination section 109c determines the tableware placement positions in accordance with general rules. The general rules concerning the tableware placement positions of tableware M1 for a main dish, tableware M2 for a side dish (bread), tableware M3 for a side dish (coffee), tableware E1 (knife), and tableware E2 (fork) would suggest you to place the tableware M1 at the center of the table T, place the tableware M2 on the left of the tableware M1, place the tableware M3 on the right of the tableware M1, place the tableware E1 at the rightmost position, and place the tableware E2 at the leftmost position. Therefore, the determination section 109c determines the detailed arrangement positions for arranging the tableware M1, the tableware M2, the tableware M3, the tableware E1, and the tableware E2 in the above-described positional relationship.

For example, in accordance with a range that permits the target user U11 to move his/her body and is based on the physical information regarding the target user U11, the determination section 109c determines the tableware placement positions. For example, as the arm length of the target user U11 is "L11 (cm)," the determination section 109c identifies an arm movable range based on the arm length "L11 (cm)," and determines the tableware placement positions within the identified arm movable range. In the example of FIG. 1, the determination section 109c identifies a region R11-1 as a right-arm movable range, and identifies a region R11-2 as a left-arm movable range. In other words, the target user U11 in a seated position is unable to reach the outside of the region R11-1 even when his/her right arm is fully extended. Further, the target user U11 in a seated position is unable to reach the outside of the region R11-2 even when his/her left arm is fully extended.

After identifying the above-mentioned ranges (regions), the determination section 109c determines the tableware placement positions within a range including both the region R11-1 and the region R11-2 in accordance with the general rules. More specifically, as illustrated in FIG. 1, the determination section 109c determines the tableware arrangement positions within the range including the region R11-1 and the region R1-2 so as to place the tableware M1 at the center, place the tableware M2 on the left of the tableware M1, place the tableware M3 on the right of the tableware M1, place the tableware E1 at the rightmost position, and place the tableware E2 at the leftmost position. In the example of FIG. 1, as the target user U11 is "right-handed," the determination section 109c has determined a placement of the tableware E1 at the rightmost position and place the tableware E2 at the leftmost position. However, in a case where the target user U11 is "left-handed," for example, the determination section 109c determines a placement of the tableware E1 at the leftmost position place the tableware E2 at the rightmost position.

(Determination Processing Pattern 2)

Figure 5:
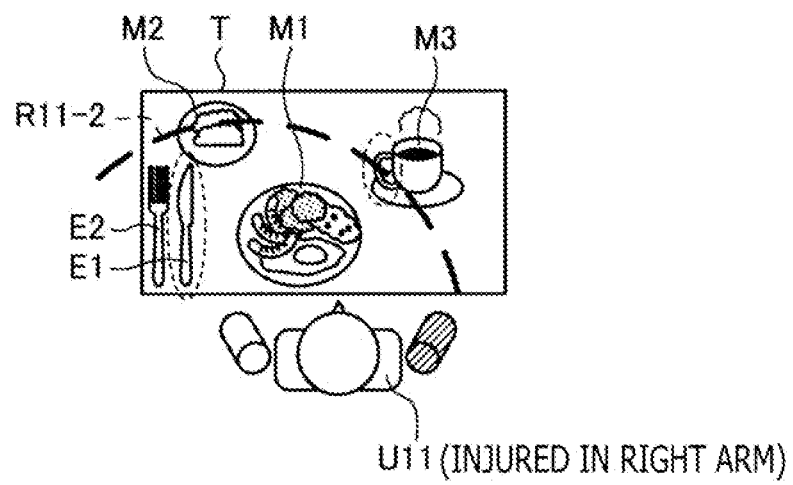
FIG. 5 is a diagram illustrating an example of information processing (pattern 2) according to an embodiment of the present disclosure.

Next, determination processing performed in a case where the identification section 109a has identified (determined) that the target user is injured or otherwise physically disabled will be described as determination processing pattern 2. FIG. 5 is a diagram illustrating an example of information processing (pattern 2) according to the present disclosure.

The identification section 109a identifies the physical information regarding the target user U11 on the basis of imaged information acquired by an imaging operation. The example of FIG. 5 assumes that the identification section 109a has identified, on the basis of the imaged information, the age, the arm length, and the dominant arm of the target user U11 who is determined to be "in his/her twenties," has an arm length of "L11 (cm)," and is "right-handed." Further, it is assumed that the identification section 109a has identified, on the basis of the imaged information, that the target user U11 is "injured in his/her right arm." It should be noted that the identification section 109a is also able to identify the physical information on the basis of not only the imaged information but also speech information collected by the microphone 103. For example, in a case where the target user U11 has uttered, "My right arm is injured," the identification section 109a identifies that the target user U11 is "injured in his/her right arm."

In the above case, the determination section 109c first determines that considerations need to be taken into account regarding the tableware placement positions because the target user U11 is "injured" (physically disabled). After determining that considerations need to be taken into account regarding the tableware placement positions, the determination section 109c determines the tableware placement positions by preferentially taking into account the considerations necessary for the tableware placement positions while considering the general rules within a possible range. In this instance, it is assumed that the target user U11 is unable to freely move his/her right arm due, for instance, to a bandage wound around his/her right arm.

Here, in the example of FIG. 5, the right arm of the target user U11 is movable within the region R11-1 and the left arm is movable within the region R11-2, as is the case with FIG. 1. In such a state, only the right arm is movable within a region of the region R11-1 that excludes the region R11-2 (a region where the tableware M3 and the tableware E1 are placed). Thus, the target user U11 is unable to reach such a region with his/her left arm. As such being the case, if the tableware M3 and the tableware E1 are placed in such a region, it is necessary for the target user U11 to pick up the tableware M3 and the tableware E1 with his/her right arm.

However, if the target user U11 is injured in his/her right arm, the target user U11 is unable to perform such a pick-up operation. In other words, if the tableware is placed as illustrated in FIG. 1 in a case where the target user U11 is injured in his/her right arm, the target user U11 is unable to pick up the tableware M3 and the tableware E1.

For the above reasons, the determination section 109c determines the arrangement positions depicted, for example, in FIG. 5. More specifically, as the arm length of the target user U11 is "L11 (cm)," the determination section 109c identifies the region R11-1 as the right-arm movable range on the basis of the arm length "L11 (cm)," and identifies the region R11-2 as the left-arm movable range. After the above identification, the determination section 109c does not consider the region R11-1, which is the right-arm movable range, and determines the tableware placement positions within the region R11-2, which is the left-arm movable range. For example, as illustrated in FIG. 5, the determination section 109c determines the arrangement positions within the region R11-2 so as to place the tableware M1 in front of the center, place the tableware M2 on the left rear of the tableware M1, and place the tableware M3 on the right rear of the tableware M1. In this instance, the determination section 109c also determines the orientation of tableware to be placed on the table. For example, the determination section 109c determines the orientation of the tableware M3 so that the handle of a coffee cup, which is the tableware M3, is placed on the left side.

Further, as illustrated in FIG. 5, the determination section 109c determines the arrangement positions within the region R11-2 so that the tableware E1 and the tableware E2 are placed in front of the left arm. In the example of FIG. 1, the determination is made in accordance with the general rules so as to place the tableware E1 at the rightmost position and place the tableware E2 at the leftmost position. However, in the example of FIG. 5, the determination section 109c determines so that, within the region R11-2, the tableware E1 is to be placed to the right of the tableware E2.

When the above-described arrangement positions are adopted, the target user U11 is able to handle all the tableware items easily with his/her left arm. Further, the target user U11 is not forced to use his/her injured right arm and is thus able to comfortably have a meal. In other words, even in a case where the target user is physically disabled, the robot apparatus 100 is able to determine the optimal tableware placement positions where the target user enjoys a meal.

(Overview (2) of Determination Section 109c)

Further, the determination section 109c determines the object arrangement positions on the basis of the conditions of objects. For example, the determination section 109c determines the object arrangement positions on the basis of the conditions of the objects and of the physical structure of the target user. For example, the determination section 109c determines the object arrangement positions on the basis of the condition of an object, namely, at least one of the temperature of the object, the shape of the object, the size of the object, or the contents of the object. Determination processing patterns 3 and 4, which are associated with the above determination processing, will now be described.

(Determination Processing Pattern 3)

As mentioned earlier, the identification section 109a is able to identify not only the physical information but also the condition of an object. For example, on the basis of an order received from the target user, the identification section 109a not only identifies the tableware to be used for each ordered food, but also identifies the temperature, shape, size, and contents (i.e., food) of the identified tableware filled with food. The temperature of the identified tableware filled with food may be substituted by the temperature of the food itself.

Figure 6:
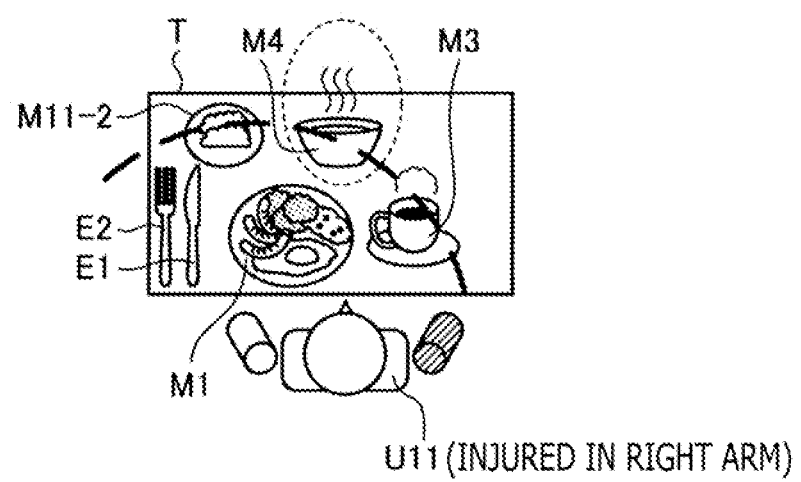
FIG. 6 is a diagram illustrating an example of information processing (pattern 3) according to an embodiment of the present disclosure.

Determination processing in a case where the identification section 109a has determined that the contents (i.e., food) of tableware have a high temperature will now be described as determination processing pattern 3. FIG. 6 is a diagram illustrating an example of information processing (pattern 3) according to the present disclosure. The example of FIG. 6 assumes that a high-temperature soup dish is additionally ordered, and that tableware M4 for the soup dish is to be placed in addition to the tableware M1 to M3, the tableware E1, and the tableware E2. It should be noted that FIG. 6 depicts an example in which determination processing pattern 3 is added to the determination processing (pattern 2) for a case where the target user U11 is injured in his/her right arm. However, the contents of determination processing pattern 3 remain unchanged even in a case where, for example, the target user U11 is healthy (pattern 1).

On the basis of imaged information acquired by an imaging operation, the identification section 109a identifies the physical information regarding the target user U11. The example of FIG. 6 assumes that the identification section 109a has identified, on the basis of the imaged information, the age, the arm length, and the dominant arm of the target user U11 who is determined to be "in his/her twenties," has an arm length of "L11 (cm)," and is "right-handed." Further, it is assumed that the identification section 109a has identified, on the basis of the imaged information, that the target user U11 is "injured in his/her right arm."

In the above case, the determination section 109c does not consider the region R11-1, which is the right-arm movable range, and determines the tableware placement positions within the region R11-2, which is the left-arm movable range. For example, as is the case with the example of FIG. 5, the determination section 109c determines the arrangement positions within the region R11-2 so as to place the tableware M1 in front of the center, place the tableware M2 on the left rear of the tableware M1, and place the tableware M3 on the right rear of the tableware M1.

If, in the above instance, for example, a significantly steamy, hot dish or a grilled or other dishes characterized by sizzling meat juice is to be placed at hand of the target user U1, it is conceivable that the target user U1 is troubled by heat when he/she reaches out a hand for the other dishes. Therefore, within the region R11-2, the determination section 109c determines a position distant by a predetermined distance or more from the target user U1 as the placement position of the tableware M4. In the example of FIG. 6, the determination section 109c determines a position near the boundary line of the region R11-2 as the placement position of the tableware M4. For example, as depicted in FIG. 6, the determination section 109c first determines the arrangement positions of the tableware M1 to M3, the tableware E1 and E2, and then determines, as the placement position of the tableware M4, a position that is included in the remaining space within the region R11-2 and in the vicinity of the boundary line of the region R11-2.

When the arrangement positions are determined as described above, the target user U11 is able to have a meal safely. In other words, the robot apparatus 100 is able to provide an environment where the target user is able to have a meal safely.

(Determination Processing Pattern 4)

As mentioned earlier, the identification section 109a is also able to identify not only the physical information but also the condition of an object. For example, on the basis of an order received from the target user, the identification section 109a identifies the tableware to be used for each ordered food.

Figure 7:
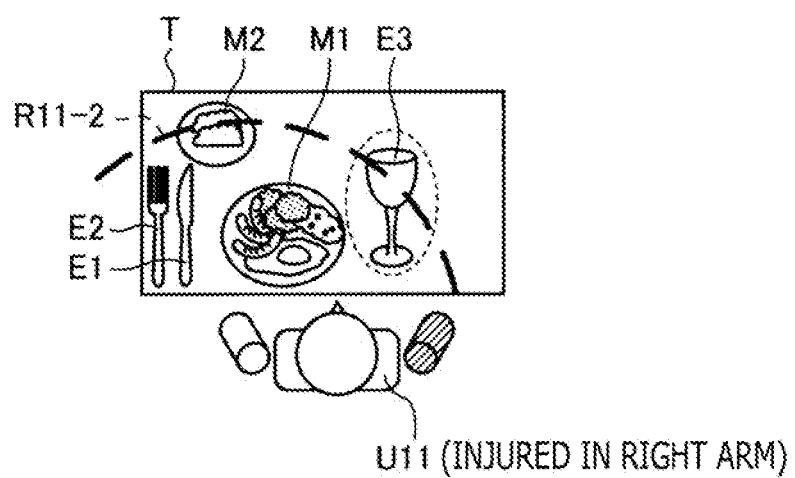
FIG. 7 is a diagram illustrating an example of information processing (pattern 4) according to an embodiment of the present disclosure.

Determination processing in a case where the identification section 109a has identified a tall wine glass as one tableware item will now be described as determination processing pattern 4. FIG. 7 is a diagram illustrating an example of information processing (pattern 4) according to the present disclosure. More specifically, the example of FIG. 7 assumes that, on the basis of an order from the target user U11, the identification section 109a has identified tableware M1, tableware M2, tableware E1, tableware E2, and tableware E3 (wine glass). It should be noted that FIG. 7 depicts an example in which determination processing pattern 4 is added to the determination processing (pattern 2) for a case where the target user U11 is injured in his/her right arm. However, the contents of determination processing pattern 4 remain unchanged even in a case (pattern 1) where, for example, the target user U11 is healthy (pattern 1).

On the basis of imaged information acquired by an imaging operation, the identification section 109a identifies the physical information regarding the target user U11. The example of FIG. 7 assumes that the identification section 109a has identified, on the basis of the imaged information, the age, the arm length, and the dominant arm of the target user U11 who is determined to be "in his/her twenties," has an arm length of "L11 (cm)," and is "right-handed." Further, it is assumed that the identification section 109a has identified, on the basis of the imaged information, that the target user U11 is "injured in his/her right arm."

In the above case, the determination section 109c does not consider the region R11-1, which is the right-arm movable range, and determines the tableware placement positions within the region R11-2, which is the left-arm movable range. For example, as is the case with the example of FIG. 5, the determination section 109c determines the arrangement positions within the region R11-2 so as to place the tableware M1 in front of the center, place the tableware M2 on the left rear of the tableware M1, and place the tableware E1 and E2 in front of the left arm.

If, in the above case, a wine glass or other tall tableware is placed too close to a hand of the target user, there is a risk of causing an accident in which an elbow of the target user hits such tall tableware. Therefore, on the basis of the physical structure of the target user U11, the determination section 109c calculates, for example, the position of a left elbow within the region R11-2, which is the left-arm movable range, in a case where the target user U11 extends his/her left arm. In a case where the tableware E3, which is a wine glass, is placed at the calculated position, there is a risk of causing an accident. Therefore, the determination section 109c determines, as the placement position of the tableware E3, a position other than the position of the left elbow within the region R11-2, that is, a position within the region R11-2 at which the left elbow is not placed. For example, as depicted in FIG. 7, the determination section 109c first determines the arrangement positions of the tableware M1 and M3, and tableware E1 and E2, and then determines, as the placement position of the tableware E3, a position that is included in the remaining space within the region R11-2 and unreachable by the left elbow.

It should be noted that, in a case where different tableware is placed behind the tall tableware E3, the target user may run the risk of toppling the tableware E3 when picking up the different tableware. Therefore, the determination section 109c is able to determine the tableware placement positions in consideration of such risk as well. For example, the determination section 109c does not determine a position in front of the tableware M1 or the tableware M2 as the placement position of the tableware E3, but determines the placement position of the tableware E3 as depicted in FIG. 7 so that no other tableware is positioned behind the tableware E3.

When the arrangement positions are determined as described above, the target user U11 is able to have a meal safely. In other words, the robot apparatus 100 is able to provide an environment where the target user is able to have a meal safely.

(Overview (3) of Determination Section 109c)

Further, the determination section 109c determines the object arrangement positions on the basis of a range that permits the target user to move his/her body and is based on the physical information. For example, in a case where a plurality of target users exists, the determination section 109c determines the object arrangement positions in accordance with the relationship between the plural target users. For example, the determination section 109c determines the object arrangement positions on the basis of the physical information regarding a higher-level target user in the relationship and of the physical information regarding a lower-level target user in the relationship. More specifically, the determination section 109c determines the object arrangement positions within a range that permits the higher-level user to move his/her body and that excludes a range where the lower-level user is able to move his/her body. Determination processing pattern 5, which is associated with the above determination processing, will now be described.

(Determination Processing Pattern 5)

Figure 8:
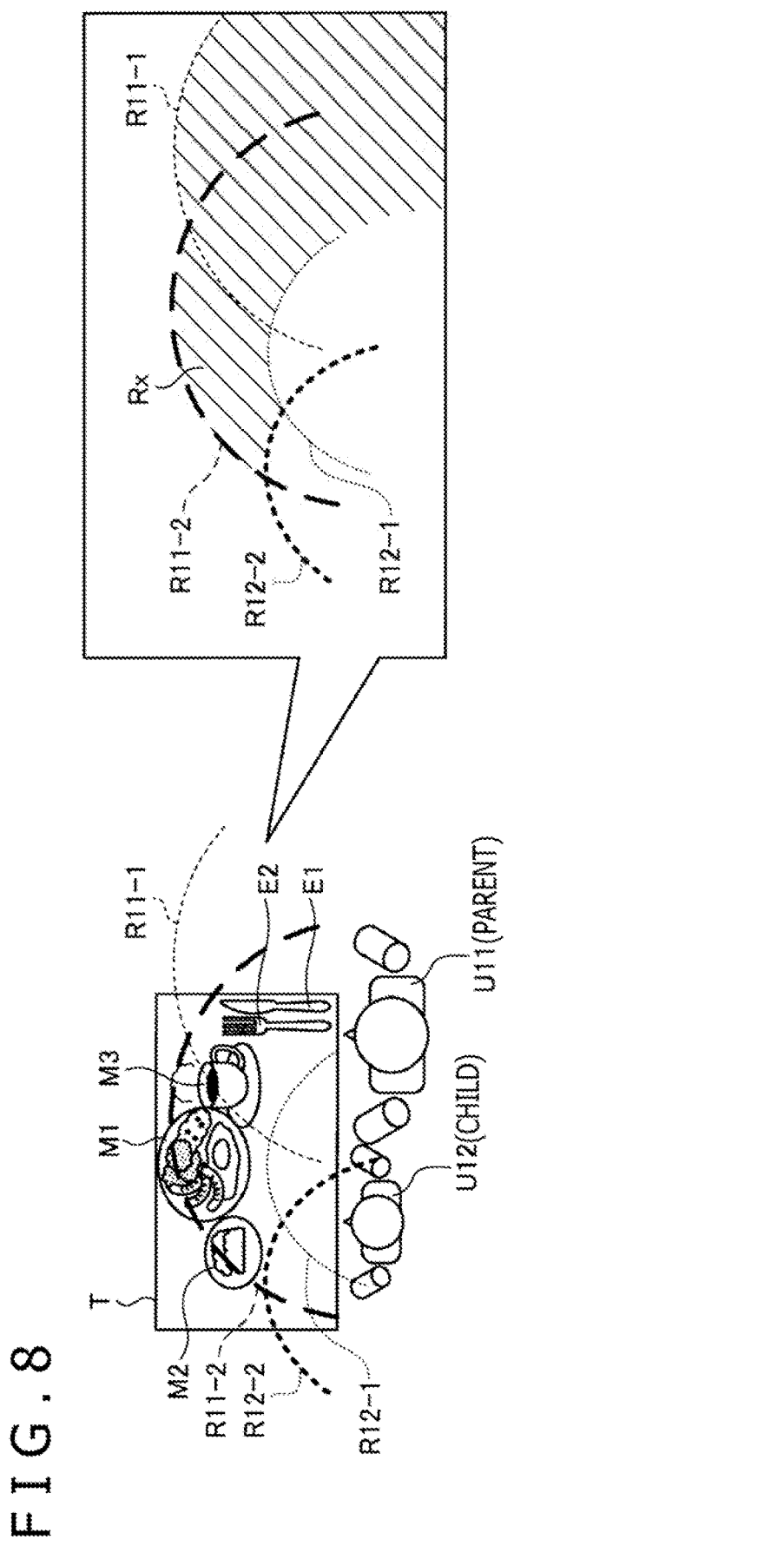
FIG. 8 is a diagram illustrating an example of information processing (pattern 5) according to an embodiment of the present disclosure.

FIG. 8 is a diagram illustrating an example of information processing (pattern 5) according to the present disclosure. First of all, the relationship between a plurality of target users is, for example, a parent-to-child relationship or a caregiver-to-care recipient relationship. In the parent-tochild relationship, a parent (guardian) is at a higher level than a child (infant), and the child (infant) is at a lower level than the parent (guardian). Meanwhile, in the caregiver-to-care recipient relationship, a caregiver is at a higher level than a care recipient, and the care recipient is at a lower level than the caregiver. For example, in a case where a plurality of target users exists, the identification section 109a is also able to perform a process of identifying (estimating) the relationship between the plural target users on the basis of imaged information acquired by an imaging operation. It should be noted that such a process may be performed by a processing section other than the identification section 109a. It should also be noted that the identification section 109a may identify (estimate) the relationship between the plural target users on the basis of speech information acquired by collecting a sound.

In the above example, when a plurality of target users visits a restaurant together, the identification section 109a identifies the relationship between the plural target users. Let us assume, for example, that an adult target user U11 and an infant target user U12 have visited a restaurant together and taken a seat at a table T. In such a case, the identification section 109a identifies the relationship between the target user U11 and the target user U12 on the basis of their appearance and conversation. Let us assume, for example, that the identification section 109a has identified that the target user U11 and the target user U12 are in a parent-to-child relationship, and that the target user U11 is a parent at a higher level while the target user U12 is a child at a lower level.

Further, in the above state, the identification section 109a identifies the physical information regarding the target users U11 and U12 on the basis of imaged information acquired by an imaging operation. The example of FIG. 8 assumes that the identification section 109a has identified, on the basis of the imaged information, the age, the arm length, and the dominant arm of the target user U11 who is determined to be "in his/her twenties," has an arm length of "L11 (cm)," and is "right-handed." Further, it is assumed that the identification section 109a has identified, on the basis of the imaged information, the age, the arm length, and the dominant arm of the target user U12 who is determined to be "two years old," has an arm length of "L12 (cm)," and is "right-handed." Furthermore, the identification section 109a has identified, on the basis of the imaged information, that the target users U11 and U12 are "healthy" because no particular injury or other health problems have been identified. Moreover, the example of FIG. 8 assumes that the identification section 109a has identified, on the basis of an order from the target user U11, a placement of the tableware M1 to M3, and the tableware E1 and E2 on the table, as is the case with the example of FIG. 1.

In the above case, the determination section 109c determines the tableware placement positions based on a range that permits the target user U11 to move his/her body on the basis of the physical information regarding the target user U11 and based on a range that permits the target user U12 to move his/her body on the basis of the physical information regarding the target user U12. In the example of FIG. 8, as regards the target user U11, the determination section 109c identifies the region R11-1 as the right-arm movable range and identifies the region R11-2 as the left-arm movable range. Further, as regards the target user U12, the determination section 109c identifies a region R12-1 as the right-arm movable range and identifies a region R12-2 as the left-arm movable range.

The target user U12 is "two years old" (an infant). Therefore, if tableware filled with food is placed within the reach of the target user U12, that is, within a range including the region R12-1 and the region R12-2, the target user U12 may run an increased risk, for example, of touching hot tableware or toppling tableware. Consequently, the determination section 109c determines the arrangement positions within a range that is reachable by a hand of the target user U11 but not reachable by a hand of the target user U12. More specifically, the determination section 109c determines the tableware placement positions within a region Rx. The region Rx is within a range including the regions R11-1 and R11-2, which are reachable by a hand of the target user U11, and without a region including the regions R12-1 and R12-2, which are reachable by a hand of the target user U12. The target user U12 is unable to reach the region Rx with his/her hand.

For example, as illustrated in FIG. 8, the determination section 109c determines the arrangement positions within the region Rx so as to place tableware M1 at the center, place tableware M2 on the left of the tableware M1, place tableware M3 on the right of the tableware M1, and place neighboring tableware E1 and E2 in front of the target user U11.

Adopting the above arrangement positions permits the target user U12 to avoid the risk of getting burned and toppling or dropping tableware. Further, this reduces stress on the target user U11. In other words, the robot apparatus 100 is able to determine the tableware placement positions that permit the target users to enjoy eating safely and comfortably.

It should be noted that, in a case where the target users include, for example, a user who is unable to freely move his/her body at his/her own will such as an infant, the identification section 109a determines the style of tableware use, for example, by determining the use of a straw as one tableware item or inserting a straw into a covered cup when the straw is to be used. Further, this processing may be performed by the determination section 109c.

(Other Determination Processing)

Five different determination processing patterns have been described thus far. However, the determination section 109c may perform the determination processing in a pattern other than those described above. The following describes this point. In the foregoing examples, the determination section 109c determines the object arrangement positions. However, the determination section 109c may determine the positional relationship between objects on the basis of target user's operability on the objects, and determine the object arrangement positions on the basis of the determined positional relationship.

In a case where, for example, tableware items are arranged without a gap in between, it may be difficult even for a healthy person to pick up a tableware item. The reason is that neither a finger nor a hand can be inserted between one tableware item and another because the tableware items are arranged without a gap in between. In such a case, an effective way is to predict, if possible, the size of a hand of a target user, determine the positional relationship so as to create a gap, in accordance with the predicted size of the hand, between one tableware item and another, and determine tableware arrangement positions on the basis of the determined positional relationship. Further, even in a case where the size of a hand of the target user is unpredictable, the positional relationship between the tableware items may be determined so as to create the gap in accordance with the typical size of a hand, for example.

Consequently, referring to the example of FIG. 1, the determination section 109c identifies the positional relationship between the tableware M1 to M3, and determines (calculates) the size of a necessary gap (gap width) between the tableware M1, M2, and M3 on the basis of the predicted size of the hand of the target user U11. The determination section 109c then creates a gap having a size equal to or larger than the determined gap size (gap width), and determines the tableware arrangement positions as illustrated, for example, in FIG. 1. It should be noted that the determination section 109c is able to calculate the size of a hand on the basis of, for example, imaged information representative of a captured image of the target user U11. However, the method of calculating the size of a hand is not limited to the above one. Any other method may be used to calculate the size of the hand.

It should be noted that arranging tableware on the table T in a simple manner without considering the gap between tableware items is easy even for the manipulator 106 (robot hand), which is inferior to humans in hand dexterity. For example, the manipulator 106 is able to arrange tableware without a gap in between by sequentially placing tableware items from the end of the table T. In some cases, however, it is difficult for the manipulator 106, which is inferior to humans in hand dexterity, to arrange the tableware items on the table T in accordance with the gap size determined by the determination section 109c. Accordingly, in a case where the tableware items are arranged on the table T in accordance with the gap size determined by the determination section 109c, the later-described execution section 109h performs a simulation for determining whether or not the target user U11 is able to easily grasp the tableware. Then, in a case where the result of the simulation indicates that the target user U11 is unable to easily grasp the tableware, for example, the determination section 109c recalculates the gap size.

Further, the determination section 109c may determine the tableware arrangement positions on the basis of history information regarding a target user. For example, the physical information identified regarding the target user is stored in the storage section 108a. Therefore, in a case where the physical information identified when the target user previously visited a restaurant is stored in the storage section 108a, the determination section 109c may determine the tableware arrangement positions on the basis of the previously stored physical information.

Further, the storage section 108b stores arrangement information indicative of the tableware arrangement positions determined for each target user. Therefore, instead of newly determining the tableware arrangement positions on the basis of the physical information, the determination section 109c may refer to the storage section 108b and adopt previously determined tableware arrangement positions or fine-tune previously determined tableware arrangement positions and adopt the fine-tuned tableware arrangement positions as the current tableware arrangement positions.

Further, the determination section 109c is also able to determine the tableware arrangement positions by using a learning result (model) obtained through machine learning. This point will be described later.

Furthermore, the determination section 109c may allow the identification section 109a to perform an identification process (determination processing). For example, on the basis of the physical information regarding a target user, the determination section 109c may determine (identify) objects (tableware) to be delivered to the target user or the style of use (usage) of objects to be delivered to the target user.

(Output Control Section 109d)

The output control section 109d provides output control for outputting (displaying), to a user, arrangement information indicative of arrangement positions determined by the determination section 109c. For example, the output control section 109d provides output control for outputting (displaying), to a terminal apparatus of the user, arrangement information indicative of arrangement positions determined by the determination section 109c. For example, in a case where the robot apparatus 100 has a display screen (display), the output control section 109d causes the display screen to display the arrangement information indicative of the arrangement positions determined by the determination section 109c. Referring to the example of FIG. 1 for explanatory purposes, when the tableware placement positions are determined for the target user U11, the output control section 109d causes the display screen to display a conceptual diagram (indicative of eating utensils and plates filled with food that are placed on the table T in accordance with the determined tableware placement positions) exactly as depicted in FIG. 1.

Further, in a case where, for example, the restaurant SH1 lends the instruction apparatus 50 to the target user as a predetermined terminal apparatus, the output control section 109d may cause the display screen of the instruction apparatus 50 to display the arrangement information. In this case, the instruction apparatus 50 is the information processing apparatus used by the target user. The instruction apparatus 50 is, for example, a smartphone, a tablet terminal, a notebook PC (Personal Computer), a desktop PC, a cellular phone, or a PDA (Personal Digital Assistant). A present embodiment assumes that the instruction apparatus 50 is a tablet terminal.

In a case where an instruction regarding the arrangement positions (or a proposal regarding the arrangement positions) of objects to be delivered is received from the target user, the determination section 109c may determine the arrangement positions on the basis of the instruction (proposal). The instruction apparatus 50 is lent to the target user in order to receive the input of instruction information indicative of the contents of an instruction. A configuration of the instruction apparatus 50 will be described later.

(Reception Section 109e)

The reception section 109e receives, from a target user, an instruction regarding the arrangement positions (or a proposal regarding the arrangement positions) of objects to be delivered to the target user. For example, the arrangement positions determined by the determination section 109c do not always coincide with arrangement positions truly desired by the target user. Therefore, an effective way is to cause the display of the robot apparatus 100 or the display screen (display screen 53a) of the instruction apparatus 50 to display the arrangement positions determined by the determination section 109c, allow the target user to confirm the objects placed at the determined arrangement positions, and receive feedback based on the result of confirmation.

For example, by receiving the feedback based on the result of confirmation, the robot apparatus 100 is able to recognize the preferences (e.g., arrangement preferences) of the target user and stimulate the communication with the target user.

Consequently, when, for example, the arrangement positions determined by the determination section 109c are presented (displayed) to the target user, the reception section 109e receives an instruction regarding the presented arrangement positions and the feedback of instruction information indicative of the contents of the instruction.

Although described later, in a case where the display screen of the instruction apparatus 50 includes a touch panel, the target user is able to correct the arrangement positions by touching the touch panel and issue an instruction for switching to the corrected arrangement positions. Further, in a case where the display screen of the instruction apparatus 50 includes a projector (projector 53b), the target user is able to give an instruction on the arrangement positions, for example, by making a gesture on the arrangement information projected onto the table T by the projector.

The reception section 109e receives the instruction information instructed in the above manner through the instruction apparatus 50. Further, the reception section 109e is able to receive not only an instruction regarding the arrangement positions but also an instruction (proposal) regarding an ordered menu. For example, the reception section 109e receives instructions regarding changes in the type of tableware filled with ordered food, the layout of dishes (e.g., the positional relationship between different foods arranged on one plate), disliked food, and allergy-causing food.

Subsequently, the robot apparatus 100 gives the above instructions to a cook. In accordance with the instructions, the cook prepares food and arranges the prepared food on a plate. Accordingly, the robot apparatus 100 is able to increase the degree of freedom for creating orderable tableware placement schemes and thus provide enhanced satisfaction to customers.

Furthermore, the reception section 109e is able to receive instructions regarding, for example, the way of cutting food, the length of noodles (e.g., pasta), eating and drinking utensils (e.g., chopsticks), and heating perishables thoroughly. This enables the robot apparatus 100 to comply with a detailed target user request, for example, for preparing finely cut food that is easily eaten by an infant, cutting pasta to short lengths to permit a customer unable to properly use forks to easily eat the pasta with chopsticks, bringing chopsticks instead of a knife and a fork, or heating fish thoroughly because raw fish is one of the customer's disliked foods. As a result, the robot apparatus 100 is able to provide enhanced satisfaction to customers.

Moreover, the robot apparatus 100 is able to learn, through machine learning, the preferences of the target user regarding, for example, arrangement positions, tableware, and food on the basis of instructions received by the reception section 109e as described above. Such machine learning is performed, for example, by the learning section 109g.

(Operation Control Section 109f)

The operation control section 109f provides control over the operations of the robot apparatus 100. For example, the operation control section 109f controls the robot apparatus 100 so that the robot apparatus 100 arranges objects at the arrangement positions determined by the determination section 109c. For example, the operation control section 109f controls the robot apparatus 100 so that the robot apparatus 100 places tableware at the tableware placement positions determined by the determination section 109c.

For example, in the example of FIG. 1, the operation control section 109f controls the robot apparatus 100 so that the robot apparatus 100 grasps the tableware, moves to the table T of the target user U11, and places the grasped tableware at the determined tableware placement positions. For example, if, in the example of FIG. 1, a determination has been made to place tableware items one by one in order from tableware M1, tableware M2, tableware M3, tableware E1, tableware E2, the operation control section 109f controls the robot apparatus 100 so that the robot apparatus 100 places the tableware items in the above order. The operation control section 109f controls, for example, the manipulator 106 and the drive section 107 so as to operate the robot apparatus 100 in the above manner.

Figure 9:
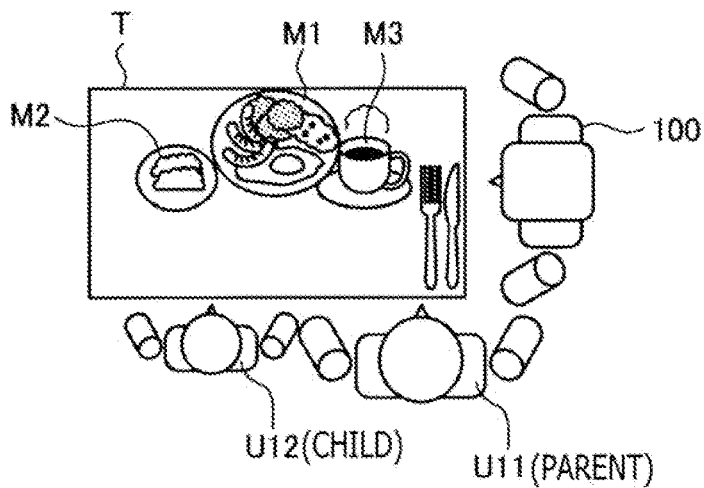
FIG. 9 is a diagram illustrating an example of motion control of the robot apparatus according to an embodiment of the present disclosure.

FIG. 8 depicts an example in which in a case where a plurality of target users exists, the determination section 109c determines object arrangement positions on the basis of the relationship between the target users. More specifically, FIG. 8 is used to depict determination processing that is performed in a case where a target user U11 is accompanied by a target user T12 who is an infant to be protected (taken care of) by the target user U11. In a case where a plurality of existing target users is in a higher level-to-lower level relationship as described above, the operation control section 109f controls the robot apparatus 100 so that the robot apparatus 100 first approaches a higher-level target user, takes an order, and performs tableware placement work. This point will be described with reference to FIG. 9. FIG. 9 is a diagram illustrating an example of motion control of the robot apparatus 100 according to an embodiment of the present disclosure.

For example, in a case where the robot apparatus 100 approaches the target user U12, who is an infant, that is, approaches the left side of the table T, the working robot apparatus 100 runs the risk of coming into contact with the target user U12. Further, there is a risk that the target user U12 recklessly touches the robot apparatus 100. Consequently, the operation control section 109f controls the motion of the robot apparatus 100 so that the robot apparatus 100 approaches the target user U11, that is, the right side of the table T as depicted in FIG. 9. For example, the operation control section 109f controls the drive section 107. The robot apparatus 100 is able to implement, for example, an operation in the interest of safety of the target users.

(Learning Section 109g)

The learning section 109g performs learning regarding the physical information. For example, the learning section 109g generates a model MD1, as the physical information, by learning the relationship between the external appearance of a target user and the physical information regarding the target user. The learning section 109g generates the model MD1 by learning, for example, the typical relationship between the external appearance of a target user and the physical characteristics of the target user. For example, the learning section 109g generates the model MD1, which is a predictive model for, upon receiving the input of external physical characteristics of the target user (e.g., chronological imaged information captured by the camera 102 and known object information regarding an area around the target user including an item worn by the target user), outputting (predicting) the physical information regarding the target user (e.g., height, sitting height, an arm length, arm injury, age, hand size, and a dominant arm).

FIG. 1 depicts an example in which the identification section 109a identifies the physical information by analyzing the imaged information and speech information regarding the target user U11. However, the identification section 109a may identify (predict) the physical information regarding the target user U11 by applying the imaged information regarding the target user U11 represented by the model MD1. In such a case, the identification section 109a need not analyze the imaged information or speech information. This makes it possible to identify the physical information promptly within a shorter period of time when, for example, an order is received from the target user U11.

Figure 10:
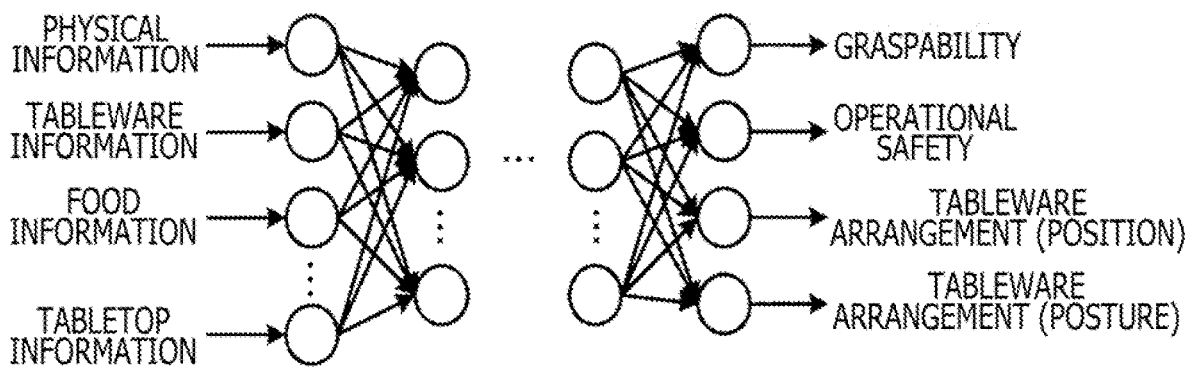
FIG. 10 is a conceptual diagram illustrating an example of machine learning according to an embodiment of the present disclosure.

Further, the learning section 109g generates a model MD2 by learning through machine learning target user's operability on objects. For example, the learning section 109g generates the model MD2 by learning through machine learning, on the basis of the size of a hand of a target user, the positional relationship between tableware items (e.g., the size of a gap between tableware items) that provides the target user with ease of operation. This point will now be described with reference to the example of FIG. 10. FIG. 10 is a conceptual diagram illustrating an example of machine learning according to the present disclosure.

As illustrated in FIG. 10, the learning section 109g generates the model MD2, which is a predictive model for, upon receiving, for example, the input of physical information regarding the target user (e.g., height, sitting height, an arm length, arm injury, age, hand size, and a dominant arm), outputting (predicting) information indicative of whether or not the target user is able to easily grasp delivered objects, indicative of whether or not a grasping operation is safe, and indicative of preferable tableware arrangement (arrangement positions and orientations) for tableware grasping. As illustrated in FIG. 10, the learning section 109g is able to generate the model MD2 that is based on not only the input of physical information but also the input of tableware information, food information, and tabletop information. It should be noted that the learning section 109g may generate the model MD2 which can input a plurality of pieces of tableware information simultaneously.

(Execution Section 109h)

The execution section 109h executes an operation plan for evaluating the target user's operability on objects in a situation where the objects are delivered and placed at the arrangement positions determined by the determination section 109c. For example, the execution section 109h executes an operation plan for evaluating the target user's operability on the objects in a case where the objects are delivered and placed at the arrangement positions determined by the determination section 109c. The target user's operability is, for example, indicative of whether or not the target user is able to easily grasp the delivered objects, indicative of whether or not a grasping operation is safe, and indicative of preferable tableware orientation for tableware grasping. For example, in a case where tableware items are arranged on the table T in accordance with the gap size determined by the determination section 109c, the execution section 109h executes an operation plan for determining whether or not the target user is able to easily grasp the tableware items.

For example, the execution section 109h is able to execute an operation plan for applying (updating) the robot apparatus 100 to the physical structure and position of the target user. More specifically, the execution section 109h returns to an operation plan for evaluating whether or not a manipulator having the same hand size or arm size as the target user and having the same joint structure as the target user is able to easily grasp a target object (tableware) while the trunk of the robot apparatus 100 is at a position where the target user is seated. The execution section 109h is able to apply any method to such an operation plan. The execution section 109h is able to use an open source such as OpenRAVE (Open Robotics Automation Virtual Environment). The execution section 109h then executes the operation plan in the above manner to simulate whether the objects are in a proper positional relationship (in terms, for example, of the size of a gap between tableware items).

Further, the execution section 109h may apply the result of machining learning to the operation plan. For example, the execution section 109h performs simulation on the basis of information that is outputted when various kinds of information is inputted to the model MD2 learned by the learning section 109g. Moreover, the determination section 109c corrects the object arrangement positions on the basis of the result of simulation based on the operation plan.

3. Configuration of Instruction Apparatus (Configuration (1) of Instruction Apparatus)

Figure 11:
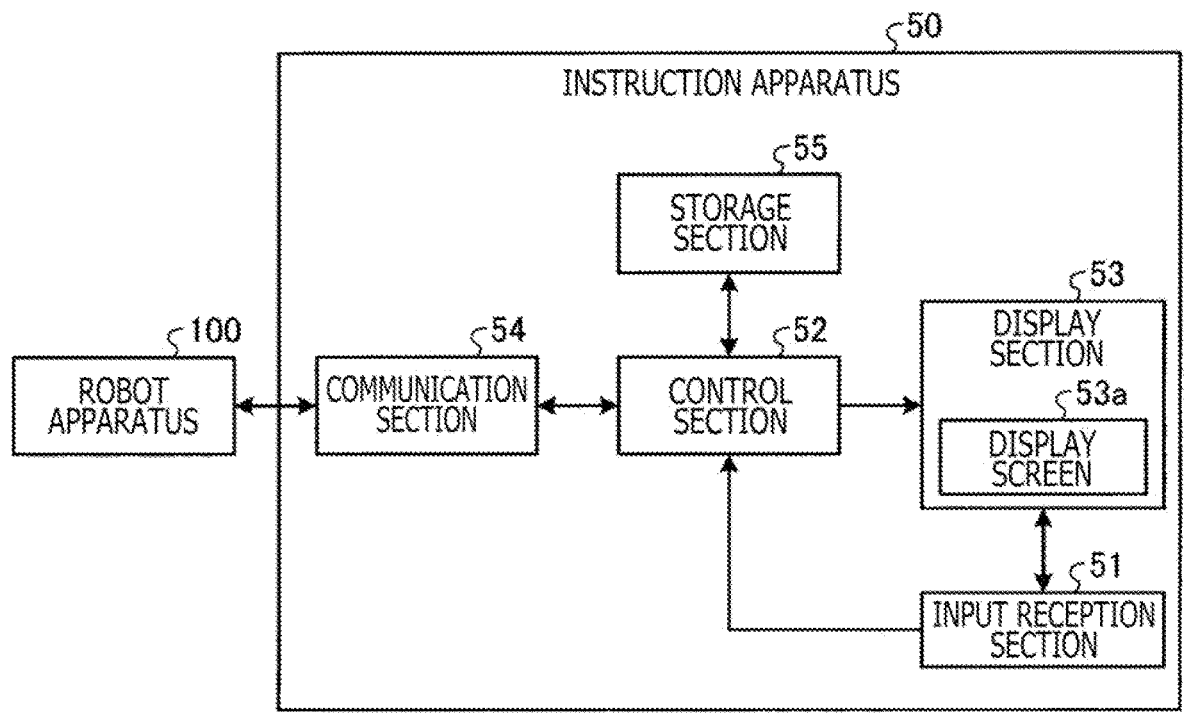
FIG. 11 is a schematic diagram illustrating a functional configuration for controlling an instruction apparatus according to an embodiment of the present disclosure.

A configuration of the instruction apparatus 50 according to an embodiment of the present disclosure will now be described with reference to FIG. 11. As mentioned earlier, the instruction apparatus 50 is an information processing apparatus used by a target user. For example, in a case where the target user is to issue a proposal, request, or instruction regarding, for example, arrangement positions, tableware, and food, the target user inputs the contents of an instruction by using the instruction apparatus 50. FIG. 11 is a schematic diagram illustrating a functional configuration for controlling the instruction apparatus 50 according to an embodiment of the present disclosure. As illustrated in FIG. 11, the instruction apparatus 50 includes an input reception section 51, a control section 52, a display section 53, a communication section 54, and a storage section 55.

(Input Reception Section 51)

The input reception section 51 receives an input of various kinds of information from the target user. For example, the input reception section 51 receives instruction information regarding a target user's instruction regarding the arrangement positions determined by the determination section 109c of the robot apparatus 100. Further, for example, the input reception section 51 receives instructions regarding an ordered menu and tableware in addition to an instruction regarding the arrangement positions. The information received by the input reception section 51 is transmitted to the reception section 109e of the robot apparatus through the communication section 54. The input reception section 51 includes, for example, a touch panel and a keyboard. A present embodiment assumes that the instruction apparatus 50 is a table terminal. Therefore, a touch panel is adopted for the input reception section 51 in a present embodiment.

(Control Section 52)

The control section 52 controls information regarding the robot apparatus 100. For example, the control section 52 provides display control for causing the display section 53 to display arrangement information indicative of arrangement positions determined by the determination section 109c of the robot apparatus 100. The control section 52 generates, for example, an arrangement image indicative of arrangement positions, supplies the generated arrangement image to the display section 53, and causes the display screen 53a to display the arrangement image.

(Display Screen 53a)

The display section 53 displays information supplied by the control section 52. In the example of FIG. 11, a so-called common display screen 53a, such as the display screen of a display apparatus, is adopted as the display section 53. Therefore, the display screen 53a displays, for example, an arrangement image supplied by the control section 52.

(Communication Section 54)

The communication section 54 is implemented, for example, by an NIC. The communication section 54 is then wiredly or wirelessly connected to a network and, for example, transmits and receives information to and from the robot apparatus 100. For example, the communication section 54 transmits information received by the input reception section 51 to the reception section 109e of the robot apparatus 100.

(Storage Section 55)

The storage section 55 stores information received by the input reception section 51. The storage section 55 may store the information received by the input reception section 51 as text or as an image.

Figure 13:
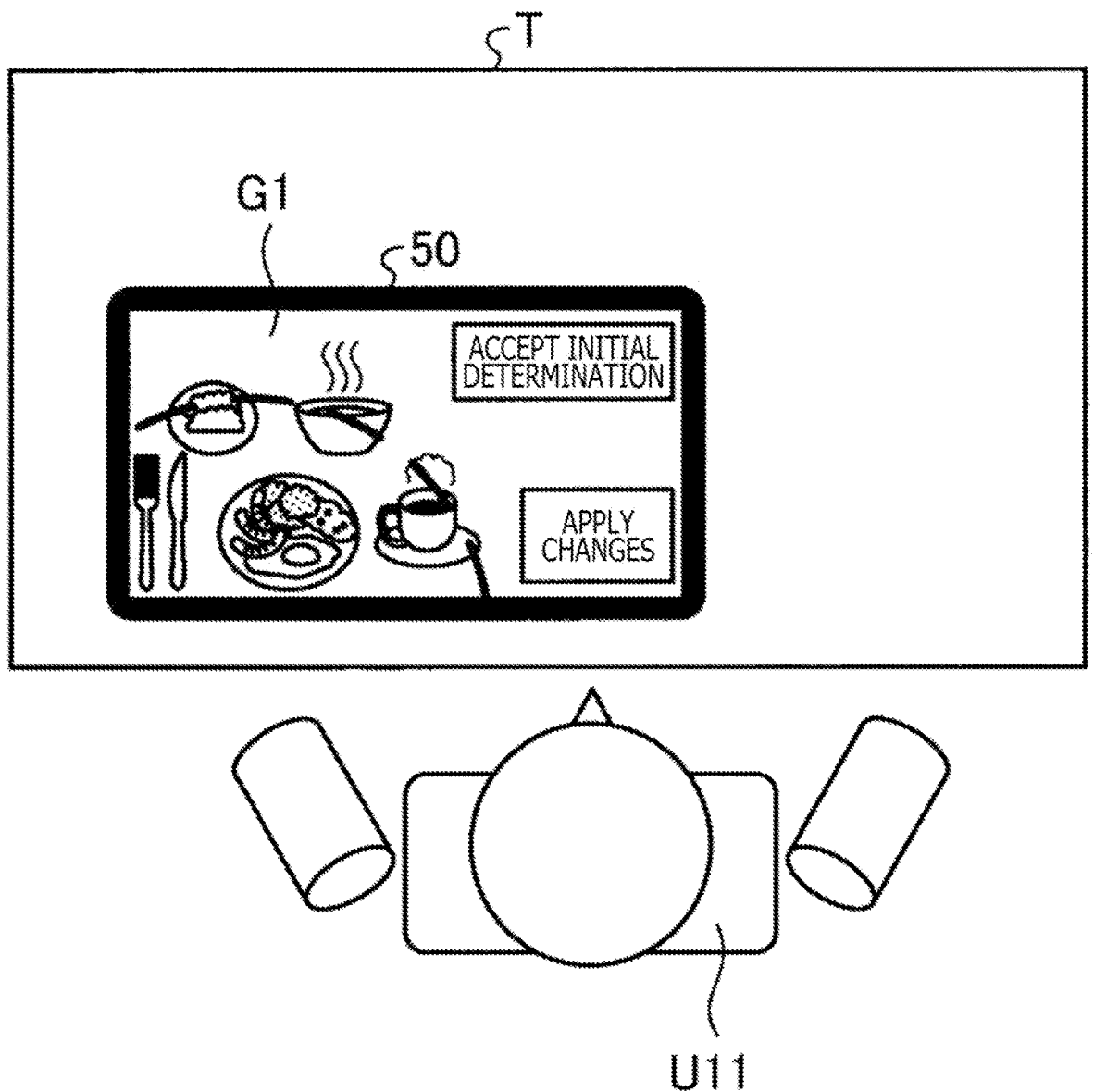
FIG. 13 is a diagram illustrating an example of an arrangement image displayed on a display screen according to an embodiment of the present disclosure.

An example of an instruction operation performed by a target user will now be described with reference to FIG. 13. FIG. 13 is a diagram illustrating an example of an arrangement image displayed on the display screen 53a according to the present disclosure. In the example of FIG. 13, the control section 52 generates image information G1 indicative of tableware placement based on arrangement positions determined by the determination section 109c, and causes the display screen 53a to display the generated image information G1. For example, the control section 52 generates the image information G1 that is controlled to permit the target user to freely move an image of a tableware item by touching the image of the tableware item included in the image information G1. When the target user is a target user U11 who wants to issue an instruction for correcting the arrangement positions indicated by the image information G1 in accordance with his/her preferences, the target user U11 touches a target tableware image and then swipes the target tableware image to a desired position. In a case where, for example, tableware filled with bread is to be moved further to the left, the target user U11 touches the associated tableware image, swipes the associated tableware image to the left until it reaches a desired position, and stops touching the associated tableware image.

When the above-described change to the desired position terminates, the target user U11 presses an "APPLY CHANGES button" displayed in the lower right corner of the display screen 53a. This completes the target user U11's input of an instruction (proposal) regarding the arrangement positions. Further, the input reception section 51 receives, as instruction information, the image information G1 that is changed to represent a change applied to the arrangement positions by the target user's pressing the "APPLY CHANGES button". Furthermore, the input reception section 51 stores the changed image information G1 in the storage section 55. The communication section 54 acquires the changed image information G1 from the storage section 55 and transmits the changed information G1 to the reception section 109e of the robot apparatus 100. In this case, for example, on the basis of the instruction information received by the reception section 109e, the determination section 109c corrects the arrangement positions on the basis of the instruction from the target user U11.

It should be noted that the example of FIG. 13 depicts an "ACCEPT INITIAL DETERMINATION button," which is displayed in the upper right corner of the display screen 53a. In a case where, for example, no particular instruction needs to be issued regarding the arrangement positions determined by the robot apparatus 200, the target user U11 may press the "ACCEPT INITIAL DETERMINATION button." Further, in such a case, the robot apparatus 100 determines a placement of the tableware at initially determined arrangement positions. Furthermore, although not depicted in FIG. 13, the control section 52 is able to cause the display screen 53a to display a question in text form (e.g., "any request on the cooking method?") or an input field in order to receive, for example, instructions regarding an ordered menu and tableware.

As described above, the robot apparatus 100 is able to receive various kinds of feedback on determined arrangement positions from a target user. Therefore, the robot apparatus 100 is capable of recognizing the preferences (e.g., arrangement preferences) of the target user and stimulating the communication with the target user.

(Configuration (2) of Instruction Apparatus)

Figure 12:
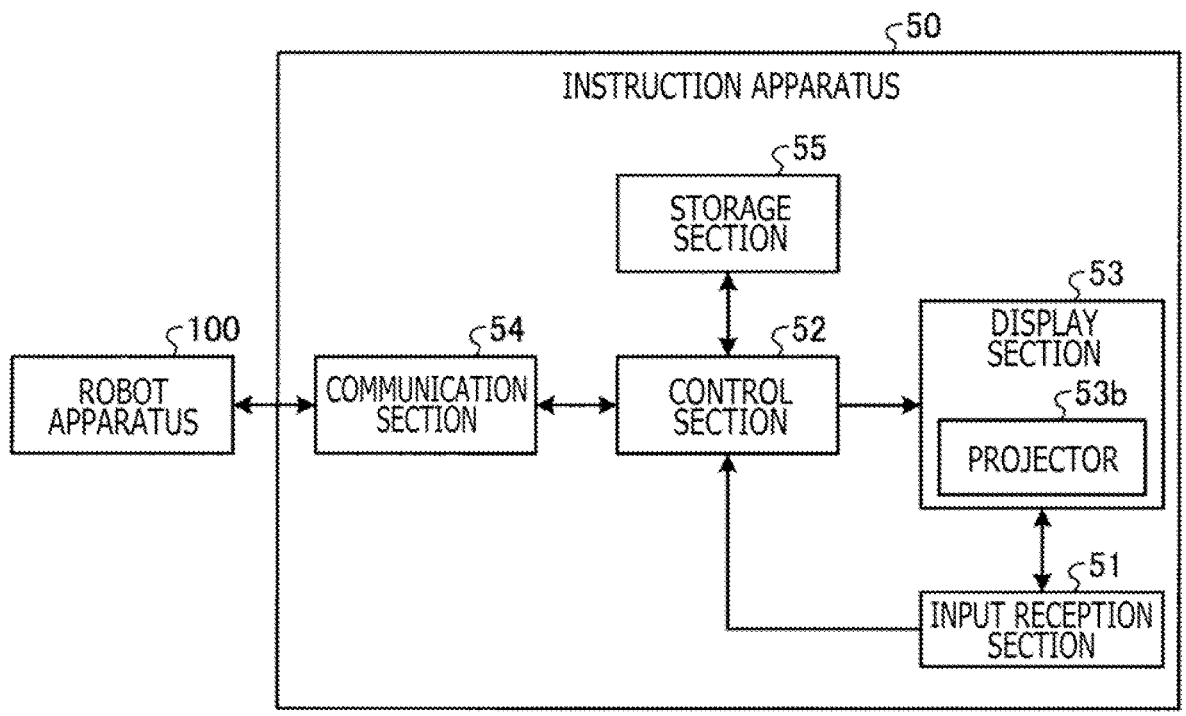
FIG. 12 is a schematic diagram illustrating a functional configuration for controlling the instruction apparatus according to an embodiment of the present disclosure.

The configuration of the instruction apparatus 50 has been described with reference to FIG. 11. However, the configuration of the instruction apparatus 50 is not limited to the exemplary configuration illustrated in FIG. 11. An alternative configuration of the instruction apparatus 50 will now be described with reference to FIG. 12. FIG. 12 is a schematic diagram illustrating a functional configuration for controlling the instruction apparatus 50 according to an embodiment of the present disclosure. It should be noted that the instruction apparatus 50 depicted in FIG. 12 has a configuration similar to the configuration illustrated in FIG. 11, except that a projector 53b is included instead of the display screen 53a. Therefore, processing sections designated by the reference signs similar to those in FIG. 11 will not be redundantly described.

(Projector 53b)

The display section 53 displays information supplied by the control section 52. In the example of FIG. 12, the projector 53b, which projects (displays) the information supplied by the control section 52 on a predetermined spot, is adopted as the display section 53. Therefore, for example, the projector 53b projects an arrangement image supplied by the control section 52 on a predetermined spot (e.g., the table T). Further, FIG. 12 assumes that a camera is adopted as the input reception section 51. Therefore, in the example of FIG. 12, it can be said that the input reception section 51 may be referred to as the imaging section 51.

An exemplary function of the projector 53b and an exemplary function of the input reception section 51 acting as a camera will now be described. FIG. 11 depicts an example in which the instruction apparatus 50 displays a tableware image included in the image information G1 and made movable to receive an instruction representative of a change operation performed on the image information G1 by the target user U11. In the example of FIG. 12, however, the projector 53b projects the image information G1, and then the input reception section 51 captures a moving image of a gesture made by the target user U11 on the projected image information G1 to receive an instruction for changing the arrangement positions.

For example, under the control of the control section 52, the projector 53b projects the image information G1, which is generated by the control section 52, on the table T. In a case where the target user U11 wants to issue, in the resulting state, an instruction for correcting the arrangement positions, which are indicated by the projected image information G1, in accordance with his/her preferences, the target user U11 makes a gesture on the tableware image. In a case where, for example, the target user U11 wants to move tableware filled with bread further to the left, the target user U11 places his/her finger on the tableware image, moves the finger leftward to a desired position, and stops the finger at the desired position. The input reception section 51 receives the instruction for changing the arrangement positions by capturing a moving image of the finger of the target user U11.

The input reception section 51 then indicates the arrangement positions specified by the gesture of the target user in the image information G1, and receives the image information G1 indicative of the user-specified arrangement positions as the instruction information. Further, the input reception section 51 stores the image information G1 in the storage section 55. The communication section 54 acquires the image information G1 from the storage section 55, and transmits the acquired image information G1 to the reception section 109e of the robot apparatus 100. In this case, on the basis of the instruction information received by the reception section 109e, for example, the determination section 109c corrects the arrangement positions in accordance with the instruction from the target user U11.

As described above, the robot apparatus 100 is able to receive various kinds of feedback on determined arrangement positions from a target user. Therefore, the robot apparatus 100 is capable of recognizing the preferences (e.g., arrangement preferences) of the target user and stimulating the communication with the target user.

4. Processing Steps

Figure 14:
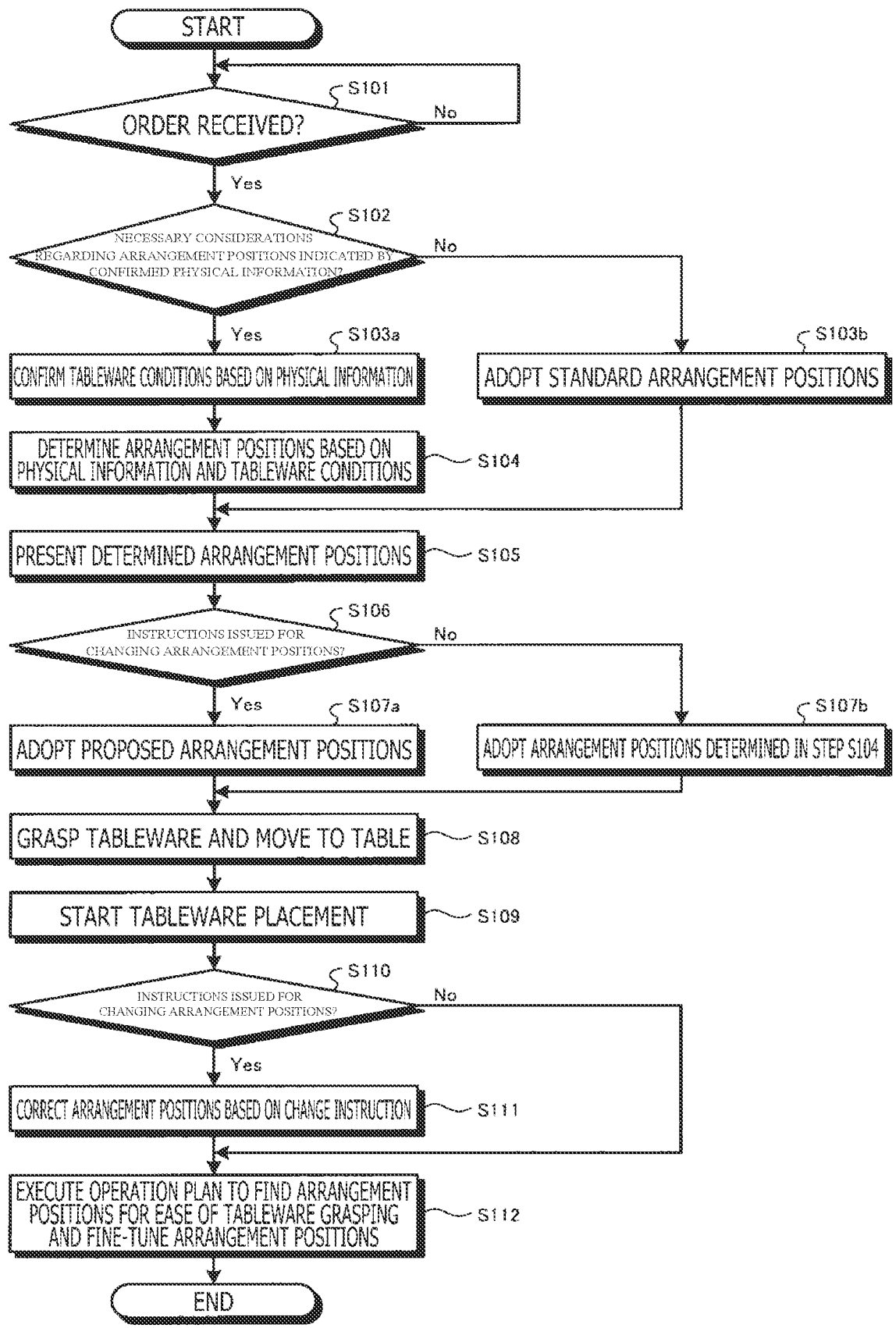
FIG. 14 is a flowchart illustrating information processing steps according to an embodiment of the present disclosure.

Information processing steps according to an embodiment of the present disclosure will now be described with reference to FIG. 14. FIG. 14 is a flowchart illustrating the information processing steps according to an embodiment of the present disclosure. For explanation purposes, FIG. 14 depicts a case where tableware arrangement positions (tableware placement positions) are to be determined at the time of tableware placement. The following description is given on the assumption that the target user U11 is a delivery target user to whom tableware is to be delivered.

First of all, the reception section 109e determines whether or not an order for a menu is received from the target user U11 (step S101). In a case where no order for a menu is received from the target user U11 ("NO" at step S101), the reception section 109e stands by until such an order is received.

In a case where the reception section 109e has determined that a menu is ordered by the target user U11 ("YES" at step S101), the identification section 109a identifies the physical information regarding the target user U11, and the determination section 109c confirms the physical information identified by the identification section 109a to determine whether or not there are necessary considerations to be taken into account as regards the tableware placement positions (step S102). It should be noted that, although not depicted in FIG. 14, the identification section 109a identifies the tableware to be filled with each ordered food item and the tableware (eating utensil) to be used for eating each ordered food item. Here, it is assumed that the identification section 109a has identified the tableware M1, the tableware M2, the tableware M3, the tableware E1, and the tableware E2 as described with reference to FIG. 1.

In a case where the determination section 109c has determined that no considerations need to be taken into account regarding the tableware placement positions ("NO" at step S102), the determination section 109c determines the tableware placement positions in accordance with the general rules (step S103b). Meanwhile, in a case where it is determined that there are necessary considerations to be taken into account as regards the tableware placement positions ("YES" at step S102), the determination section 109c confirms the conditions of the tableware (tableware conditions) based on the ordered food (step S103a). The tableware conditions include, for example, the temperature, shape, size, and contents (i.e., food) of the tableware filled with food. These conditions may be identified, for example, in step S102 by the identification section 109a. In such an instance, the determination section 109c confirms the tableware conditions identified by the identification section 109a.

Next, on the basis of the physical information regarding the target user U11 and of the tableware conditions, the determination section 109c determines the arrangement positions where the tableware M1, the tableware M2, the tableware M3, the tableware E1, and the tableware E2 are to be placed (step S104). If, for example, it is determined in step S102 that there are necessary considerations to be taken into account as regards the tableware placement positions because the target user U11 is injured in his/her right arm, the determination section 109c determines the arrangement positions of the tableware M1, tableware M2, tableware M3, tableware E1, and tableware E2 within the left-arm movable range excluding the right-arm movable range. For example, the determination section 109c determines the arrangement positions within the left-arm movable range so as to place the tableware M1 in front of the center, place the tableware M2 on the left rear of the tableware M1, and place the tableware M3 on the right rear of the tableware M1. Further, the determination section 109c determines a placement of tableware filled with hot food in the rear of the left-arm movable range. In this instance, the determination section 109c also determines the orientation of the tableware to be placed (e.g., orienting a tableware handle leftward).

Next, the output control section 109d presents, to the target user U11, the arrangement information indicative of the arrangement positions determined by the determination section 109c (step S105). For example, the output control section 109d cause a predetermined display screen to display the arrangement information. For example, the output control section 109d cause the display screen 53a of the instruction apparatus 50 possessed by the target user U11 to display the arrangement information. For example, the output control section 109d controls the control section 52 of the instruction apparatus 50 so as to display image information corresponding to the arrangement information on the display screen 53a. As described with reference to FIG. 13, the target user U11 is able to move a tableware image included in the image information to a desired position in order to issue an instruction for placing the associated tableware at the desired position. As the instruction information received by the input reception section 51, the communication section 54 of the instruction apparatus 50 transmits instruction information indicative of a change or indicative of no change to the reception section 109e of the robot apparatus 100.

The reception section 109e receives the instruction information regarding the arrangement positions, and the determination section 109c determines whether the instruction information received by the reception section 109e represents an instruction for changing the arrangement positions or an instruction for keeping the arrangement positions unchanged (step S106). In a case where the instruction information received by the reception section 109e makes a proposal for changing the arrangement positions ("YES" at step S106), the determination section 109c adopts the arrangement positions proposed by the instruction information (step S107a). More specifically, on the basis of the arrangement positions proposed by the instruction information, the determination section 109c corrects the arrangement positions determined in step S104. Meanwhile, in a case where the instruction information received by the reception section 109e represents an instruction for keeping the arrangement positions unchanged ("NO" at step S106), the determination section 109c adopts the arrangement positions determined in step S104 without changing them (step S107b). Further, the determination section 109c transmits, to the operation control section 109f, the arrangement information indicative of the arrangement positions determined (corrected) in step 3107.

The operation control section 109f controls the robot apparatus 100 so as to place the tableware at the arrangement positions determined by the determination section 109c. For example, the operation control section 109f controls the drive section 107 so as to move the main body of the robot apparatus 100 to the position of the target user U11 (e.g., the table T). Further, for example, the operation control section 109f controls the manipulator 106 so as to grasp the tableware and proceed in accordance with the arrangement positions determined by the determination section 109c. In accordance with such control, the robot apparatus 100 grasps the tableware and moves to the table T (step S108). Subsequently, upon arriving at the table T, the robot apparatus 100 begins to perform tableware placement work (step S109). In this instance, the output section 104 may output predetermined information to the target user under the control of the operation control section 109f. In a case where hot tableware to be placed, the output section 104 outputs a voice message such as "Be careful about hot tableware."

In the above instance, there may arise a case where the target user U11 watching the tableware arrangement by the robot apparatus 100 wants to change the tableware arrangement positions. For example, there may be a case where tableware set by the robot apparatus 100 cannot be handled with ease because it is actually positioned far from the target user U11. In such a case, the target user U11 issues an instruction for making a desired change to the arrangement positions. In this instance, the target user U11 is able to directly specify a change by talking to the robot apparatus 100 or by inputting the description of a change to the instruction apparatus 50. Accordingly, for example, the reception section 109e determines whether or not an instruction for changing the arrangement positions is received (step S110). In a case where no instruction is issued for changing the arrangement positions ("NO" at step S110), the reception section 109e proceeds to step S112. Meanwhile, in a case where an instruction for changing the arrangement positions is received by the reception section 109e ("YES" at step S110), the determination section 109c corrects the arrangement positions on the basis of that instruction (step S111).

Next, the execution section 109h executes the operation plan and evaluates whether or not the target user U11 is able to easily grasp tableware in a case where the tableware is placed at the arrangement positions determined by the determination section 109c or at the arrangement positions corrected as needed on the basis of an instruction from the target user U11, and then eventually, the determination section 109c fine-tunes the arrangement positions on the basis of the result of evaluation (step S112). In a case where, for example, the result of simulation performed by the execution section 109h based on the operation plan indicates that grasping is difficult, the determination section 109c calculates the size of a gap between tableware items that permits the size of a hand of the target user U11 to easily grasp the tableware. The determination section 109c then fine-tunes the current arrangement positions until they create a gap of the calculated size. The information processing and tableware placement work according to an embodiment of the present disclosure are now completed by the robot apparatus 100.

5. Hardware Configuration

Figure 15:
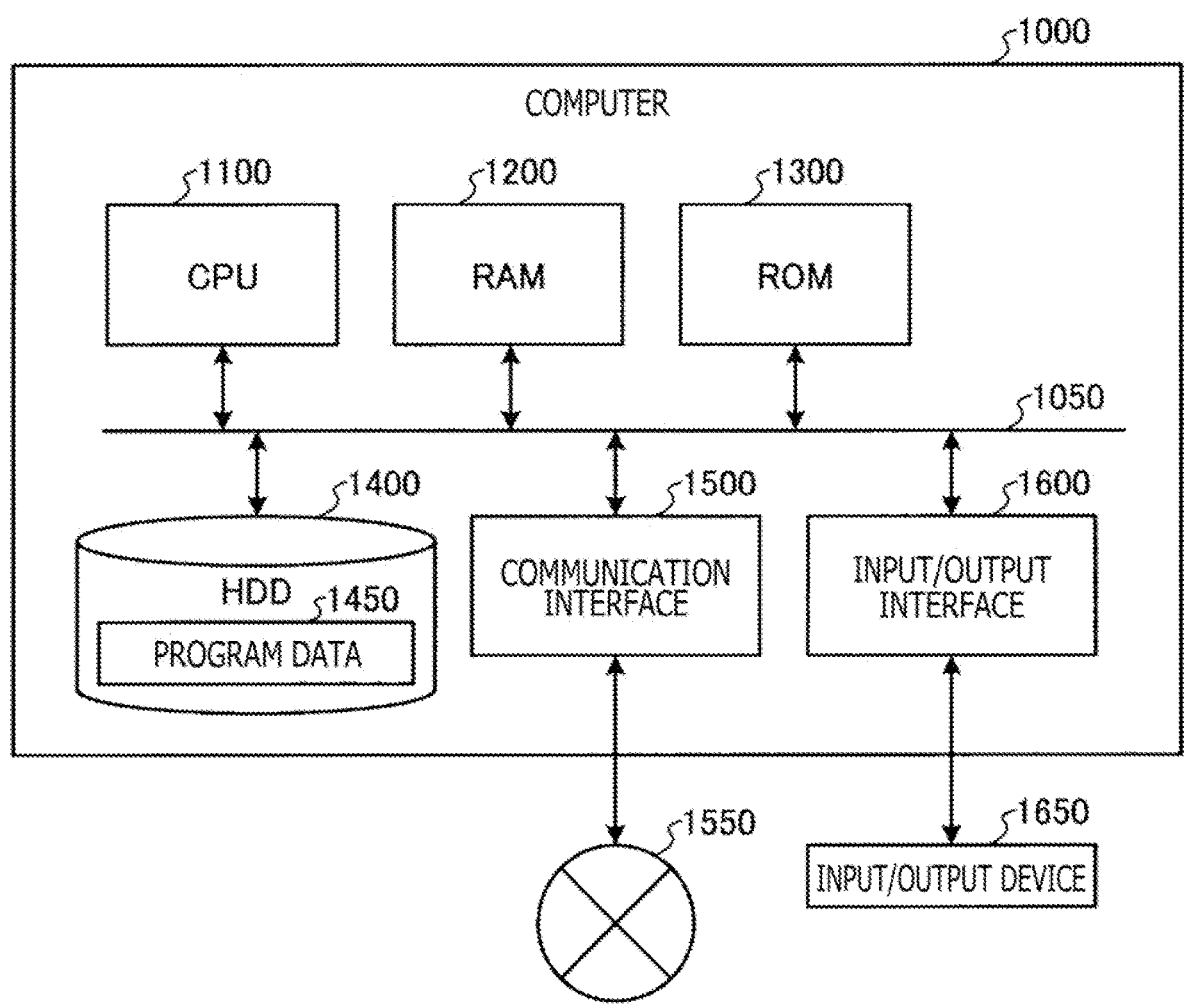
FIG. 15 is a hardware configuration diagram illustrating an example of a computer 1000 that implements the functionality of the robot apparatus 100.

The robot apparatus 100 according to an embodiment is implemented, for example, by a computer 1000 configured as illustrated in FIG. 15. FIG. 15 is a hardware configuration diagram illustrating an example of the computer 1000 that implements the functionality of the robot apparatus 100. The computer 1000 includes a CPU 1100, a RAM 1200, a ROM (Read Only Memory) 1300, an HDD (Hard Disk Drive) 1400, a communication interface 1500, and an input/output interface 1600. The various sections of the computer 1000 are connected by a bus 1050.

The CPU 1100 operates on the basis of programs stored in the ROM 1300 or the HDD 1400 to control the various sections. For example, the CPU 1100 loads the programs stored in the ROM 1300 or the HDD 1400 into the RAM 1200, and performs processing corresponding to the various programs.

The ROM 1300 stores, for example, a boot program, such as BIOS (Basic Input Output System) executed by the CPU 1100 at the startup of the computer 1000, and a program dependent on the hardware of the computer 1000.

The HDD 1400 is a computer-readable, non-transitory recording medium that records, for example, a program to be executed by the CPU 1100 and data used by such a program. More specifically, the HDD 1400 is a recording medium for recording an information processing program according to the present disclosure, which is an example of program data 1450.

The communication interface 1500 is an interface for connecting the computer 1000 to an external network 1550 (e.g., the Internet). For example, through the communication interface 1500, the CPU 1100 receives data from other equipment and transmits data generated by the CPU 1100 to other equipment.

The input/output interface 1600 is an interface for connecting an input/output device 1650 to the computer 1000. For example, the CPU 1100 receives data from an input device, such as a keyboard or a mouse, through the input/output interface 1600. Further, the CPU 1100 transmits data to an output device, such as a display, a speaker, or a printer, through the input/output interface 1600. Furthermore, the input/output interface 1600 may function as a media interface for reading, for example, a program recorded on a predetermined recording medium (media). The media include, for example, an optical recording medium, such as a DVD (Digital Versatile Disc) or a PD (Phase change rewritable Disk), a magneto-optical recording medium, such as an MO (Magneto-Optical disk), a tape medium, a magnetic recording medium, and a semiconductor memory.

In a case where, for example, the computer 1000 functions as the robot apparatus 100 according to an embodiment of the present disclosure, the CPU 1100 in the computer 1000 implements the functionality, for example, of the control section 109 by executing the information processing program loaded into the RAM 1200. Further, the HDD 1400 stores the information processing program according to the present disclosure as well as the data in the storage section 108. It should be noted that the CPU 1100 reads the program data 1450 from the HDD 1400 and executes the read program data 1450. Alternatively, however, the program data 1450 may be acquired through the external network 1550.

It should be noted that the present technology may adopt the following configurations.

(1) An information processing apparatus including:
a determination section that determines arrangement positions of objects at a time of delivery of the objects to a target user on the basis of physical information regarding a body of the target user, the target user being a user to whom the objects are to be delivered.

(2) The information processing apparatus according to (1), in which the determination section determines the arrangement positions of the objects in accordance with a range that permits the target user to move the body thereof and is based on the physical information.

(3) The information processing apparatus according to (1) or (2), in which, in a case where a plurality of the target users exists, the determination section determines the arrangement positions of the objects on the basis of a relationship between a plurality of the target users.

(4) The information processing apparatus according to any one of (1) to (3), in which the determination section determines the arrangement positions of the objects on the basis of the physical information regarding a higher-level user and of the physical information regarding a lower-level user, the higher-level user being one of the target users and is at a higher level within the relationship, the lower-level user being one of the target users and is at a lower level within the relationship.

(5) The information processing apparatus according to any one of (1) to (4), in which the determination section determines the arrangement positions of the objects in accordance with a range that permits the higher-level user to move the body thereof and that excludes a range where the lower-level user is able to move the body thereof.

(6) The information processing apparatus according to any one of (1) to (5), further including:
an acquisition section that acquires the physical information.

(7) The information processing apparatus according to any one of (1) to (6), in which the acquisition section acquires, as the physical information, information indicative of at least one of age, an arm length, a dominant arm, physical disability, or a possible upper body inclination amount.

(8) The information processing apparatus according to any one of (1) to (7), in which the acquisition section acquires, as the physical information, physical information outputted by a model, the model being generated by learning a relationship between an external appearance of the target user and the physical information regarding the target user.

(9) The information processing apparatus according to any one of (1) to (8), in which the determination section determines the arrangement positions of the objects on the basis of conditions of the objects.

(10) The information processing apparatus according to any one of (1) to (9), in which the determination section determines the arrangement positions of the objects on the basis of the conditions of the objects and of a physical structure of the target user.

(11) The information processing apparatus according to any one of (1) to (10), in which the determination section determines the arrangement positions of the objects on the basis of at least one of the conditions of the objects, namely, a temperature of the objects, a shape of the objects, a size of the objects, or contents of the objects.

(12) The information processing apparatus according to any one of (1) to (11), in which the determination section determines a positional relationship between the objects on the basis of operability of the target user on the objects, and determines the arrangement positions on the basis of the determined positional relationship.

(13) The information processing apparatus according to any one of (1) to (12), in which the determination section determines the arrangement positions of the objects on the basis of a model, the model being generated by learning through machine learning physical information regarding the target user and information regarding the arrangement of the objects.

(14) The information processing apparatus according to any one of (1) to (13), further including:
an execution section that executes an operation plan for evaluating operability of the target user on the objects in a situation where the objects are delivered and placed at the arrangement positions determined by the determination section,
in which the determination section corrects the arrangement positions of the objects on the basis of a result of simulation based on the operation plan.

(15) The information processing apparatus according to any one of (1) to (14), further including:
a reception section that receives, from the target user, an instruction regarding the arrangement positions of the objects to be delivered to the target user,
in which the determination section determines the arrangement positions of the objects on the basis of an instruction received by the reception section.

(16) The information processing apparatus according to any one of (1) to (15), in which the determination section determines, on the basis of the physical information regarding the target user, the objects to be delivered to the target user or the style of use of the objects to be delivered to the target user.

(17) The information processing apparatus according to any one of (1) to (16), further including:
a moving section that moves the objects to the arrangement positions determined by the determination section.

(18) The information processing apparatus according to any one of (1) to (17), in which the determination section determines placement positions of tableware where tableware items filled with food are to be placed as the objects.

(19) An information processing method including:
performing a process of determining arrangement positions of objects at a time of delivery of the objects to a target user on the basis of physical information regarding a body of the target user, the target user being a user to whom the objects are to be delivered.

(20) An information processing program for causing a computer to perform a process including:
determining arrangement positions of objects at a time of delivery of the objects to a target user on the basis of with physical information regarding a body of the target user, the target user being a user to whom the objects are to be delivered.

(21) An apparatus including:
a robotic arm device configured to arrange one or more objects; and
circuitry configured to
determine one or more characteristics of a user,
determine an arrangement position of each object of the one or more objects to be arranged based on the one or more determined characteristics of the user, and
initiate control of the robotic arm device to arrange each object according to the determined arrangement position of the object.

(22) The apparatus according to (21), wherein the circuitry determines the arrangement position of each object to be located within a predetermined radius from the user.

(23) The apparatus according to (21) or (22), wherein the circuitry determines the one or more characteristics of the user based on at least one of image information obtained from a captured image of the user, speech information related to the user, or a text input.

(24) The apparatus according to any one of (21) to (23), wherein the one or more characteristics of the user includes at least one of a height, a sitting height, an age, an arm length, a hand size, or a dominant arm of the user.

(25) The apparatus according to any one of (21) to (24), wherein the one or more characteristics of the user includes a health condition of the user.

(26) The apparatus according to any one of (21) to (25), wherein the health condition of the user identifies whether the user is injured or physically disabled.

(27) The apparatus according to any one of (21) to (26), wherein when the health condition of the user identifies that the user is injured, the health condition of the user further identifies which body part of the user is injured or physically disabled.

(28) The apparatus according to any one of (21) to (27), wherein the circuitry determines the arrangement position of each object in order to avoid the user having to use any body part that is injured or physically disabled.

(29) The apparatus according to any one of (21) to (28), wherein the one or more characteristics of the user includes at least one of a right-arm movable range or a left-arm movable range of the user.

(30) The apparatus according to any one of (21) to (29), wherein the one or more objects includes one or more pieces of tableware.

(31) The apparatus according to any one of (21) to (30), wherein the circuitry is further configured to identify a condition of each object, and
wherein the circuitry determines the arrangement position of each object based on the identified condition of the object.

(32) The apparatus according to any one of (21) to (31), wherein the identified condition of each object includes at least one of a temperature, a shape, a size, or contents of the object.

(33) The apparatus according to any one of (21) to (32), wherein the identified condition of each object is identified based on information acquired by one or more sensors.

(34) The apparatus according to any one of (21) to (33), wherein the apparatus includes the one or more sensors.

(35) The apparatus according to any one of (21) to (34), wherein the one or more sensors includes at least one of an imaging sensor, an audio sensor, a distance sensor, or a time of flight sensor.

(36) The apparatus according to any one of (21) to (35), wherein the one or more sensors include an imaging sensor, and
wherein the imaging sensor includes at least one of a camera, an infrared camera, or a thermographic sensor.

(37) A method of arranging one or more objects, the method including:
determining one or more characteristics of a user;
determining an arrangement position of each object of one or more objects to be arranged based on the one or more determined characteristics of the user; and
controlling a robotic arm device to arrange each object according to the determined arrangement position of the object.

(38) A non-transitory computer-readable storage medium having embodied thereon a program, which when executed by a computer causes the computer to execute a method, the method including:
determining one or more characteristics of a user;
determining an arrangement position of each object of one or more objects to be arranged based on the one or more determined characteristics of the user; and
controlling a robotic arm device to arrange each object according to the determined arrangement position of the object.

The components of each apparatus depicted above are functional and conceptual, and need not always be physically configured as depicted. In other words, the details of dispersion/integration of the various apparatuses are not limited to those depicted. The whole or part of the various apparatuses may be configured by being subjected to functional or physical dispersion/integration in a desired unit depending, for example, on various loads and uses.

While embodiments of the present application have been described in detail with reference to the accompanying drawings, such description is for illustrative purpose only. The present invention can be implemented not only by the embodiments of the disclosed invention but also by other embodiments obtained by making various modifications and improvements based on the knowledge of a person skilled in the art.

The advantages of the embodiments described in this specification are merely illustrative and not restrictive. The present invention is not limited to the described advantages and can provide additional advantages.

REFERENCE SIGNS LIST

50 Instruction apparatus
51 Input reception section
52 Control section
53 Display section
53a Display screen
53b Projector
54 Communication section
55 Storage section
100 Robot apparatus
101 Communication section
102 Camera
103 Microphone
104 Output section
105 Distance sensor
106 Manipulator
107 Drive section
108 Storage section
109 Control section
109a Identification section
109b Acquisition section
109c Determination section
109d Output control section
109e Reception section
109f Operation control section
109g Learning section
109h Execution section

The invention claimed is:
1. An apparatus comprising:
a robotic arm device configured to arrange one or more objects within a determined range of a user; and
circuitry configured to
determine one or more characteristics of the user,
determine an arrangement position of each object of the one or more objects to be arranged within the determined range of the user based on the one or more determined characteristics of the user, and
initiate control of the robotic arm device to arrange each object within the determined range of the user according to the determined arrangement position of the object,
wherein the circuitry determines the one or more characteristics of the user based on image information obtained from a captured image including the user, and wherein the circuitry determines the arrangement position of at least one of the one or more objects to be arranged within the determined range of the user further based on a relationship between the user and another user included in the captured image.

2. The apparatus according to claim 1, wherein the circuitry determines the determined range of the user is included within a predetermined radius from the user.

3. The apparatus according to claim 1, wherein the circuitry determines the one or more characteristics of the user further based on at least one of speech information related to the user or a text input.

4. The apparatus according to claim 1, wherein the one or more characteristics of the user includes at least one of a height, a sitting height, an age, an arm length, a hand size, or a dominant arm of the user.

5. The apparatus according to claim 1, wherein the one or more characteristics of the user includes a health condition of the user.

6. The apparatus according to claim 5, wherein the health condition of the user identifies whether the user is injured or physically disabled.

7. The apparatus according to claim 6, wherein when the health condition of the user identifies that the user is injured, the health condition of the user further identifies which body part of the user is injured or physically disabled.

8. The apparatus according to claim 7, wherein the circuitry determines the arrangement position of each object in order to avoid the user having to use any body part that is injured or physically disabled.

9. The apparatus according to claim 1, wherein the one or more characteristics of the user includes at least one of a right-arm movable range or a left-arm movable range of the user.

10. The apparatus according to claim 1, wherein the one or more objects comprises one or more pieces of tableware.

11. The apparatus according to claim 1,
wherein the circuitry is further configured to identify a condition of each object, and
wherein the circuitry determines the arrangement position of each object based on the identified condition of the object.

12. The apparatus according to claim 11, wherein the identified condition of each object includes at least one of a temperature, a shape, a size, or contents of the object.

13. The apparatus according to claim 11, wherein the identified condition of each object is identified based on information acquired by one or more sensors.

14. The apparatus according to claim 13, wherein the apparatus comprises the one or more sensors.

15. The apparatus according to claim 13, wherein the one or more sensors includes at least one of an imaging sensor, an audio sensor, a distance sensor, or a time of flight sensor.

16. The apparatus according to claim 13,
wherein the one or more sensors include an imaging sensor, and
wherein the imaging sensor comprises at least one of a camera, an infrared camera, or a thermographic sensor.

17. A method of arranging one or more objects, the method comprising:
determining one or more characteristics of a user;
determining an arrangement position of each object of one or more objects to be arranged within a determined range of the user based on the one or more determined characteristics of the user; and
controlling a robotic arm device to arrange each object within the determined range of the user according to the determined arrangement position of the object,
wherein the one or more characteristics of the user are determined based on image information obtained from a captured image including the user, and
wherein the arrangement position of at least one of the one or more objects to be arranged within the determined range of the user is determined further based on a relationship between the user and another user included in the captured image.

18. A non-transitory computer-readable storage medium having embodied thereon a program, which when executed by a computer causes the computer to execute a method, the method comprising:
determining one or more characteristics of a user;
determining an arrangement position of each object of one or more objects to be arranged within a determined range of the user based on the one or more determined characteristics of the user; and
controlling a robotic arm device to arrange each object within the determined range of the user according to the determined arrangement position of the object,
wherein the one or more characteristics of the user are determined based on image information obtained from a captured image including the user, and
wherein the arrangement position of at least one of the one or more objects to be arranged within the determined range of the user is determined further based on a relationship between the user and another user included in the captured image.

19. The apparatus according to claim 1,
wherein the relationship between the user and the other user is determined based on at least one of the image information or speech information.

* * * * *